(12) United States Patent
Chung et al.

(10) Patent No.: US 12,358,881 B2
(45) Date of Patent: Jul. 15, 2025

(54) PROCESSES FOR PRODUCING AMIDE COMPOUNDS, AND THEIR CRYSTALLINE AND SALT FORM

(71) Applicant: ALPHALA CO., LTD., Taipei (TW)

(72) Inventors: Cheng-Ho Chung, Taipei (TW);
Shi-Liang Tseng, Taipei (TW);
Hsiang-En Hsu, Taipei (TW)

(73) Assignee: ALPHALA CO., LTD., Taipei (TW)

( * ) Notice: Subject to any disclaimer, the term of this patent is extended or adjusted under 35 U.S.C. 154(b) by 548 days.

(21) Appl. No.: 17/908,133

(22) PCT Filed: Mar. 3, 2021

(86) PCT No.: PCT/US2021/020595
§ 371 (c)(1),
(2) Date: Aug. 30, 2022

(87) PCT Pub. No.: WO2021/178486
PCT Pub. Date: Sep. 10, 2021

(65) Prior Publication Data
US 2023/0131180 A1 Apr. 27, 2023

Related U.S. Application Data

(60) Provisional application No. 62/985,918, filed on Mar. 6, 2020.

(51) Int. Cl.
*C07D 271/107* (2006.01)

(52) U.S. Cl.
CPC ...... *C07D 271/107* (2013.01); *C07B 2200/13* (2013.01)

(58) Field of Classification Search
CPC .................................................. C07D 271/107
See application file for complete search history.

(56) References Cited

U.S. PATENT DOCUMENTS

2019/0345118 A1   11/2019   Chung et al.

FOREIGN PATENT DOCUMENTS

| JP | 2020506226 A | 2/2020 |
| TW | 201838977 A | 11/2018 |
| WO | 2018140338 A | 8/2018 |

OTHER PUBLICATIONS

Mino R. Caira, "Crystalline Polymorphism of Organic Compounds," Topics in Current Chemistry, vol. 198, Jan. 1, 1998, pp. 163-208.
Noriaki Hirayama, Organic Compound Crystallization Production Manual, 2008, pp. 17-23, 37-40, 45-51, 57-65.
Yoko Kawaguchi et al., Drug and crystal polymorphism, Journal of Human Environmental Engineering, 2002, vol. 4, No. 2, p. 310-317.
Ashizawa, Polymorphism of pharmaceuticals and the science of crystallization, 2002, p. 305-311.
Bradkey D. Anderson et al., Latest Innovative Medicinal Chemistry vol. 2, 1999, p. 347-365.
Sevim Rollas, Sevgi Karakuş, The synthesis and biological activities of 3-acyl- 2,3-dihydro-1,3,4-oxadiazole / 3-acyl-1,3,4-oxadiazoline derivatives obtained from hydrazide-hydrazones, Marmara Pharmaceutical Journal 16: 120-133, 2012.
Joseph L. Duffy, Brian A. Kirk, Zenon Konteatis, Elizabeth L. Campbell, Rutliang, Edward J. Brady,Mari Rios Candelore, Victor D. H. Ding,Guoqiang Jiang, Frank Liu, Sajjad A. Qureshi, Richard Saperstein, Deborah Szalkowski, Sharon Tong, Lauri M. Tota, Dan Xie, Xiaodong Yang, Peter Zafian, Song Zheng, Kevin T. Chapman, Bei B. Zhang and James R. Tata, Discovery and investigation of a novel class of thiophene-derived antagonists of the human glucagon receptor, Bioorganic & Medicinal Chemistry Letters. 2005.
International Search Report & Written Opinion dated Jun. 6, 2021.

*Primary Examiner* — Kamal A Saeed
(74) *Attorney, Agent, or Firm* — BACON & THOMAS, PLLC

(57) ABSTRACT

Disclosed is processes for producing amide compounds, and their crystalline and salts form. Herein, one of the amide compounds is represented by the following formula (1): which is characterized by an X-ray diffraction (XRD) pattern having peaks at about 14.2, 15.6, 16.4, 20.1, 20.5 and 21.2°±0.2° 2θ.

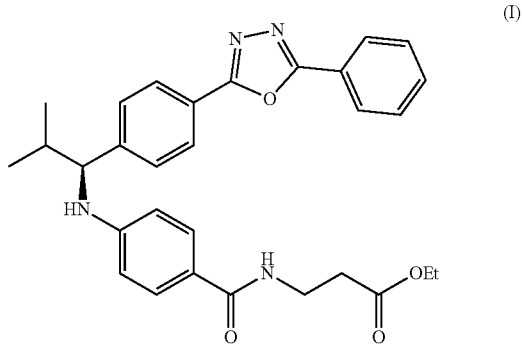

(I)

6 Claims, 11 Drawing Sheets

PROCESSES FOR PRODUCING AMIDE COMPOUNDS, AND THEIR CRYSTALLINE AND SALT FORM

This application claims the benefit of filing date of U.S. Provisional Application Ser. No. 62/985,918, filed Mar. 6, 2020, which is hereby incorporated by reference.

FIELD OF THE DISCLOSURE

The present disclosure relates to processes for producing amide compounds, and their crystalline and salt form.

BACKGROUND

ALP001E is a glucagon receptor antagonist and used for treatment of diabetes mellitus. ALP001E is a Biopharmaceutical Classification System (BCS) Class II drug which indicates poor aqueous solubility but good membrane permeability. It is stable in the solid state and not sensitive to light irradiation. However, ALP001E predominantly undergoes degradation by, hydrolytic pathways in the presence of moisture. It is also sensitive to acid or basic environments.

Because of these physicochemical and biopharmaceutical properties of ALP001E, several attempts have been made to provide different forms of ALP001E that are stable and provide desirable in vitro release and bioavailability.

Thus, it is desirable to provide a novel form of ALP001E, so that ALP001E can be applied to clinical use.

SUMMARY

The present disclosure relates to processes for producing amide compounds, and their crystal and salt form.

An aspect of the present disclosure is drawn to a crystalline form of a compound of formula (1),

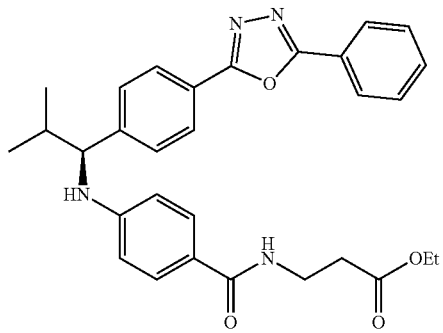

(1)

characterized by an X-ray diffraction (XRD) pattern having peaks at about 14.2, 15.6, 16.4, 20.1, 20.5 and 21.2°±0.2° 2θ.

Still within the scope of the present disclosure is a process for preparing the aforesaid crystalline form of the compound of formula (1), comprising the following steps: crystallizing the compound of formula (1) in a solvent to obtain the aforesaid crystalline form of the compound of formula (1), wherein the solvent include ethanol, isopropanol, 1-butanol, tert-butanol, ethyl acetate, butyl acetate, acetone, n-heptane, acetonitrile or a combination thereof.

Another aspect of the present disclosure is drawn to a crystalline form of a compound of formula (2),

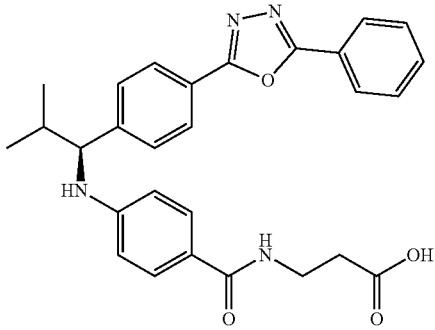

(2)

characterized by an XRD pattern having peaks at about 14.5, 18.6, 20.1, 21.8, 23.8, 25.0° 0.2° 2θ.

Still within the scope of the present disclosure is a process for preparing the aforesaid crystalline form of the compound of formula (2), comprising the following steps: crystallizing the compound of formula (2) in a solvent to obtain the aforesaid crystalline form of the compound of formula (2), wherein the solvent include methanol, ethanol, isopropanol, 1-butanol, tert-butanol, ethyl acetate, butyl acetate, acetone, acetonitrile, dicholoromethane or a combination thereof.

Another aspect of the present disclosure is drawn to a salt of the compound of formula (2). Another aspect of the present disclosure is drawn to an amorphous form of the compound of formula (1) or formula (2).

This disclosure also covers use of the crystalline form of the compound of formula (1) or formula (2), the amorphous form of the compound of formula (1) or formula (2) or the salt of the compound of formula (2) described above for reducing the glycemic level in a subject or treating disorders associated with glucagon.

Another aspect of the present disclosure is drawn to a pharmaceutical composition for reducing the glycemic level in a subject or treating disorders associated with glucagon. The pharmaceutical composition comprises: the crystalline form of the compound of formula (I) or formula (2), the amorphous form of the compound of formula (1) or formula (2) or the salt of the compound of formula (2) described above; and a pharmaceutically acceptable carrier, excipient or diluent.

This disclosure also covers use of the pharmaceutical composition for reducing the glycemic level in a subject or treating disorders associated with glucagon.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Oral solid dosage forms can be prepared by spray dried techniques; hot melt extrusion strategy, micronization, and nano milling technologies.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters, fluorocarbons, and/or other solubilizing or dispersing agents known in the art. A composition having an active compound can also be administered in the form of suppositories for rectal administration.

The carrier, the excipient and the diluent in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

Still within the scope of the present disclosure is a method of reducing the glycemic level in a subject or treating disorders associated with glucagon.

The method includes: administering to a subject in need thereof an effective amount of the crystalline form of the compound of formula (1) or formula (2), the amorphous form of the compound of formula (1) or formula (2) or the salt of the compound of formula (2) described above, or the pharmaceutical composition comprising the same.

The above-described crystalline form, amorphous form or salt of the compound of formula (1) or (2) or a pharmaceutical composition containing one or more of them can be administered to a subject orally, parenterally, by inhalation spray, topically, rectally, nasally, buccally, or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

The term "treating", "treat" or "treatment" refers to application or administration of the compound to a subject with the purpose to cure, alleviate, relieve, alter, remedy, improve, or affect the disease, the symptom, or the predisposition, "An effective amount" refers to the amount of the compound which is required to confer the desired effect on the subject. Effective amounts vary, as recognized by those skilled in the art, depending on route of administration, excipient usage, and the possibility of co-usage with other therapeutic treatments such as use of other active agents.

Still within the scope of the present disclosure is a compound of formula (3) or a salt thereof,

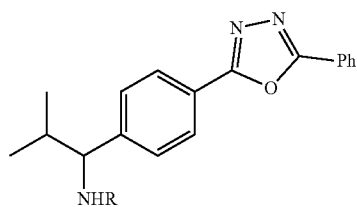

(3)

wherein R is H, $C_{1-6}$ alkyl being optionally substituted with phenyl, $C_{2-6}$ alkenyl, —S(=O)$R_1$, —P(=O)$R_2R_3$ or phenyl substituted with —COO$R_4$;
wherein $R_1$ is $C_{1-6}$ alkyl, $R_2$ is aryl, $R_3$ is aryl, and $R_4$ is H or $C_{1-6}$ alkyl.

The term "alkyl" herein refers to a straight or branched hydrocarbon group, containing 1-12 carbon atoms (e.g., $C_1$-$C_{10}$, $C_1$-$C_8$ and $C_1$-$C_6$). Examples include methyl, ethyl, n-propyl, i-propyl, n-butyl, i-butyl, and t-butyl.

The term "alkenyl" herein refers to linear or branch hydrocarbon groups with at least one double bond, and includes, for example, linear or branch $C_{2-12}$ hydrocarbon groups with at least one double bond, linear or branch $C_{2-8}$ hydrocarbon groups with at least one double bond, or linear or branch $C_{2-6}$ hydrocarbon groups with at least one double bond. Examples of the alkenyl include, but are not limited to vinyl, propenyl or butenyl.

The term "aryl" refers to a 6-carbon monocyclic, 10-carbon bicyclic, 14-carbon tricyclic aromatic ring system. Examples of aryl groups include phenyl, naphthyl, and anthracenyl.

Alkyl, alkenyl and aryl mentioned herein include both substituted and unsubstituted moieties. Possible substituents on alkenyl and aryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, alkylsulfonamino, arylsulfonamino, $C_1$-$C_{10}$ alkylimino arylimino, alkylsulfonimino, arylsulfonimino, hydroxyl, halo, thio, $C_1$-$C_{10}$ alkylthio, arylthio, alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl include all of the above-recited substituents except $C_1$-$C_{10}$ alkyl. Cycloalkyl, heterocycloalkyl, aryl, and heteroaryl can also be fused with each other.

Also within the scope of the present disclosure is a process for preparing a compound of formula (3-1), comprising the following steps:

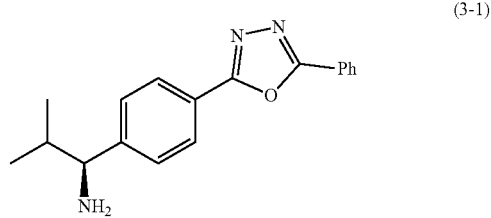

(3-1)

reacting methyl 4-formylbenzoate to form the compound of formula (3-1).

Still within the scope of the present disclosure is a process for preparing a compound of formula (1), comprising the following steps: reacting a compound of formula (3-1) to form the compound of formula (1).

Further within the scope of the present disclosure is a process for preparing a compound of formula (2), comprising the following steps: converting a compound of formula (1) into the compound of formula (2).

The details of one or more embodiments of the disclosure are set forth in the description below. Other features, objects, and advantages of the disclosure will be apparent from the description and from the claims.

DETAILED DESCRIPTION

Figure 1:
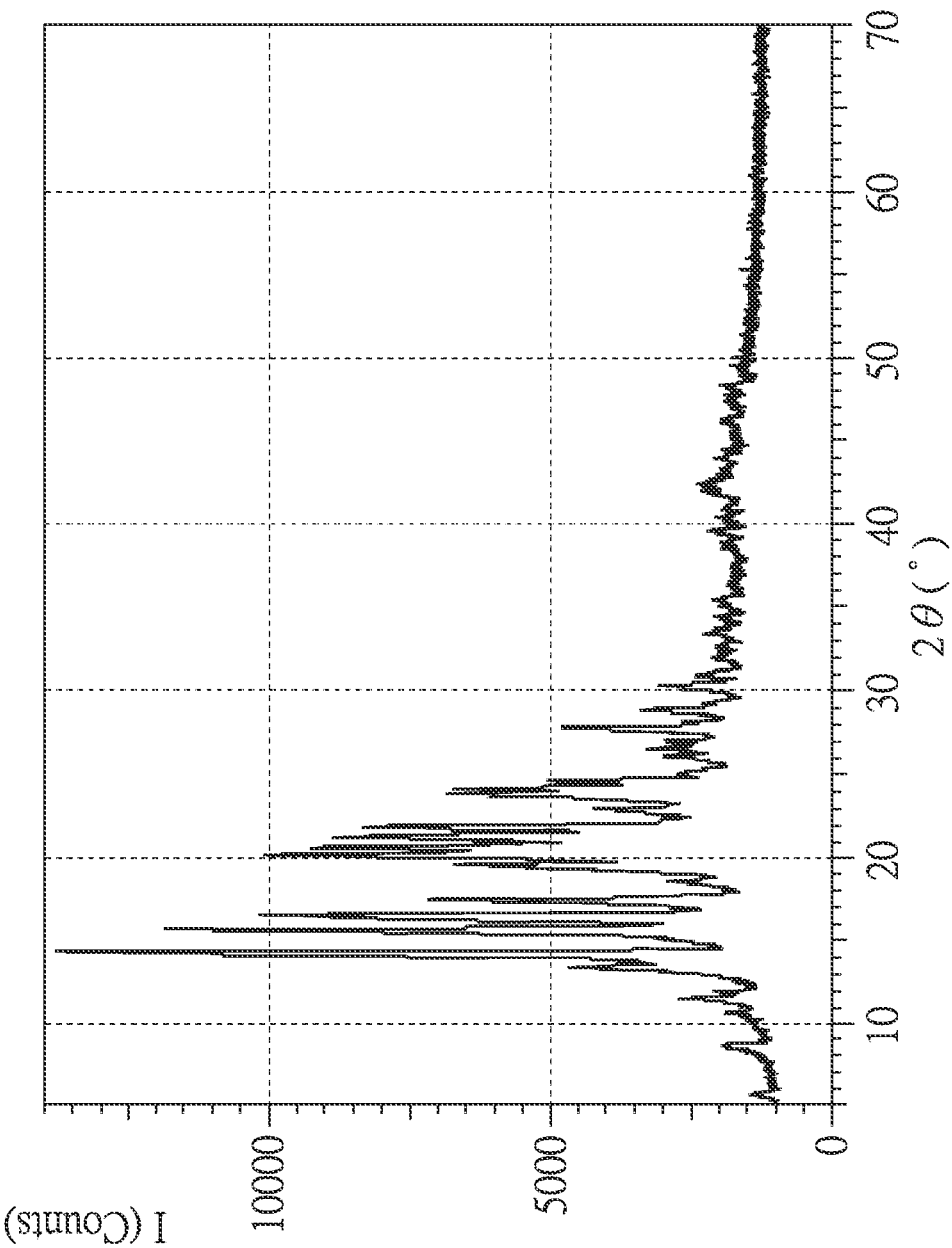
FIG. 1 shows an XRD pattern of a crystalline form of a compound of formula (1) according to Example 2 of the present disclosure.

The present disclosure provides a crystalline form of a compound of formula (1),

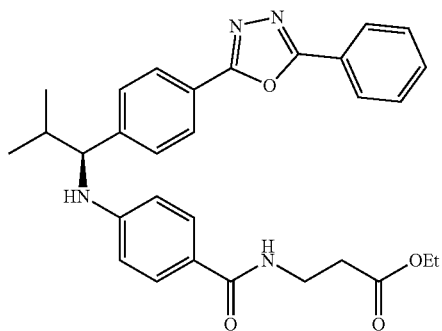

(1)

characterized by an X-ray diffraction (XRD) pattern having peaks at about 14.2, 15.6, 16.4, 20.1, 20.5 and 21.2°±0.2° 2θ.

In one embodiment, the XRD pattern of the crystalline form of the compound of formula (1) may further have peaks at about 17.4, 21.7 or 23.7°±0.2° 2θ. An exemplary crystalline form of the compound of formula (1) is characterized by the XRD pattern having peaks at about 14.2, 15.6, 16.4, 17.4, 20.1, 20.5, 21.2 and 21.7°±0.2° 2θ. Another exemplary crystalline form of the compound of formula (1) is characterized by the XRD pattern having peaks at about 14.2, 15.6, 16.4, 17.4, 20.1, 20.5, 21.2 and 23.7°±0.2° 2θ. Another exemplary crystalline form of the compound of formula (1) is characterized by the XRD pattern having peaks at about 14.2, 15.6, 16.4, 20.1, 20.5, 21.2, 21.7 and 23.7°±0.2° 2θ.

Another exemplary crystalline form of the compound of formula (1) is characterized by the XRD pattern having peaks at about 14.2, 15.6, 16.4, 17.4, 20.1, 20.5, 21.2 and 23.7°±0.2° 2θ.

In the aforesaid embodiment, the XRD pattern of the crystalline form of the compound of formula (1) may be substantially as depicted in any of FIG. 1 to FIG. 4.

In the aforesaid embodiments, the crystalline form of the compound of formula (1) may have a differential scanning calorimetry (DSC) curve having a melting endotherm peak at about 136-138° C.

The present disclosure also provides a process for preparing the aforesaid crystalline form of the compound of formula (1), comprising the following steps: crystallizing the compound of formula (1) in a solvent to obtain the aforesaid crystalline form of the compound of formula (1). The crystalline form of the compound of formula (1) can be obtained by recrystallized ethyl (S)-3-(4-((2-methyl-1-(4-(5-phenyl-1,3,4-oxadiazol-2-yl)phenyl)propyl)amino)benzamido) propanoate in a suitable solvent. Examples of the solvent may include, but are not limited to, ethanol, isopropanol, 1-butanol, tert-butanol, ethyl acetate, butyl acetate, acetone, n-heptane, acetonitrile or a combination thereof. Herein, if two or more solvents are used, the compound of formula (1) can be dissolved into a mixture of two or more solvents, or the compound of formula (1) can be dissolved into one solvent to form a mixture, followed by sequentially adding other solvents into the mixture. In addition, the compound of formula (1) may be crystallized at a temperature ranging from 0° C. to 40° C. for 2 hr to 12 hr, for example, from 5° C. to 10° C., from 15° C. to 25° C., or from 20° C. to 30° C. Furthermore, a heating step may be selectively performed before the compound of formula (1) is crystallized to facilitate the dissolution of the compound of formula (1). The temperature of the heating step may be, for example, the reflux temperature.

The present disclosure provides a crystalline form of a compound of formula (2),

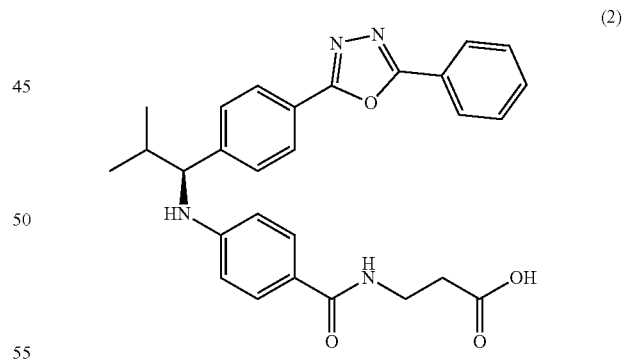

(2)

characterized by an XRD pattern having peaks at about 14.5, 18.6, 20.1, 21.8, 23.8, 25.0°±0.2° 2θ.

In one embodiment, the XRD pattern of the crystalline form of the compound of formula (2) may further have peaks at about 19.9, 22.0, 28.5 or 31.0°±0.2° 2θ. An exemplary crystalline form of the compound of formula (2) is characterized by the XRD pattern having peaks at about 14.5, 18.6, 19.9, 20.1, 21.8, 22.0, 23.8 and 25.0°±0.2° 2θ. An exemplary crystalline form of the compound of formula (2) is characterized by the XRD pattern having peaks at about 14.5, 18.6, 20.1, 21.8, 23.8, 25.0, 2.8.5 and 31.0°±0.2° 2θ.

Figure 5:
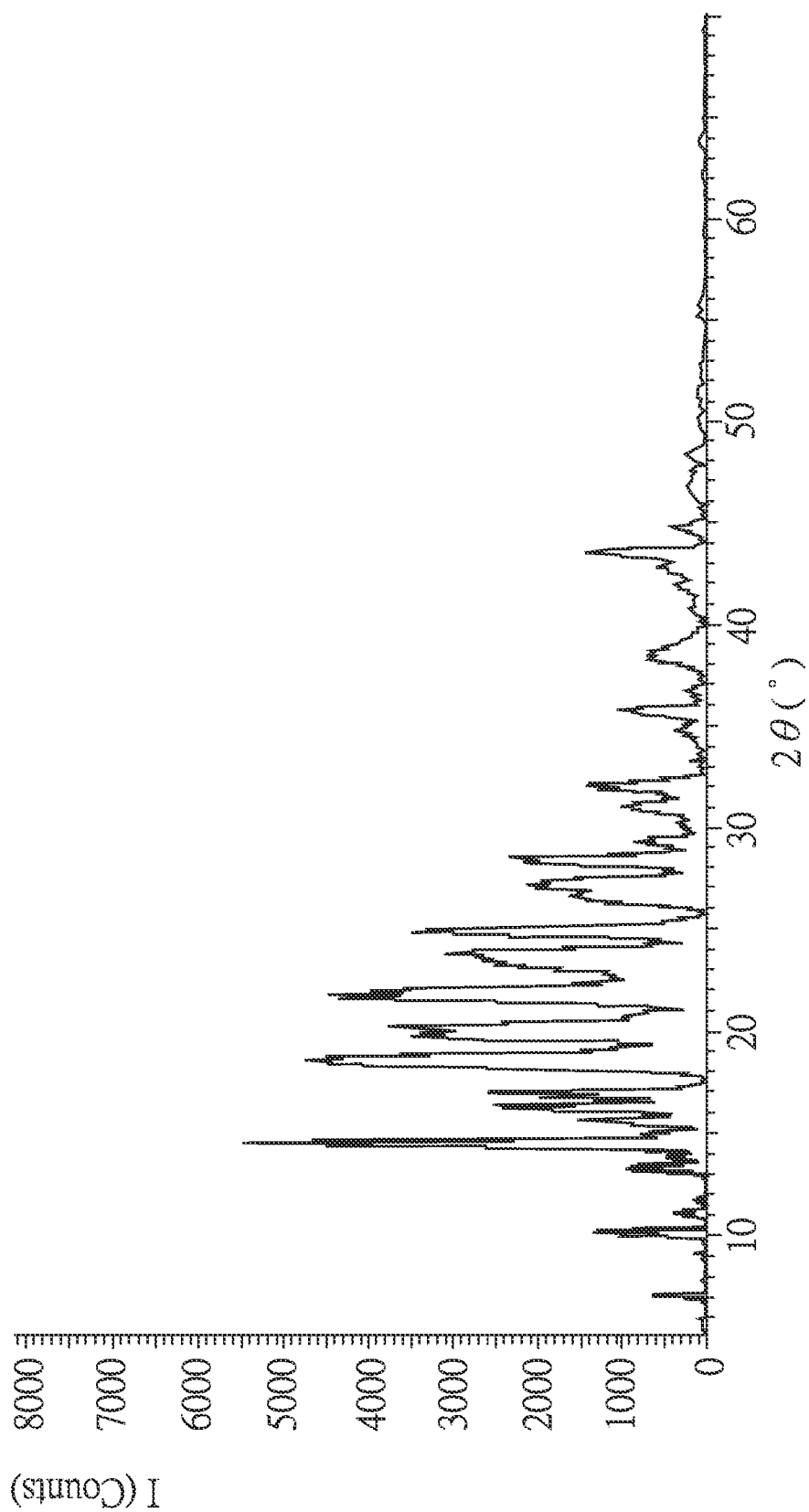
FIG. 5 shows an XRD pattern of a crystalline form of a compound of formula (2) according to Example 12 of the present disclosure.
Figure 6:
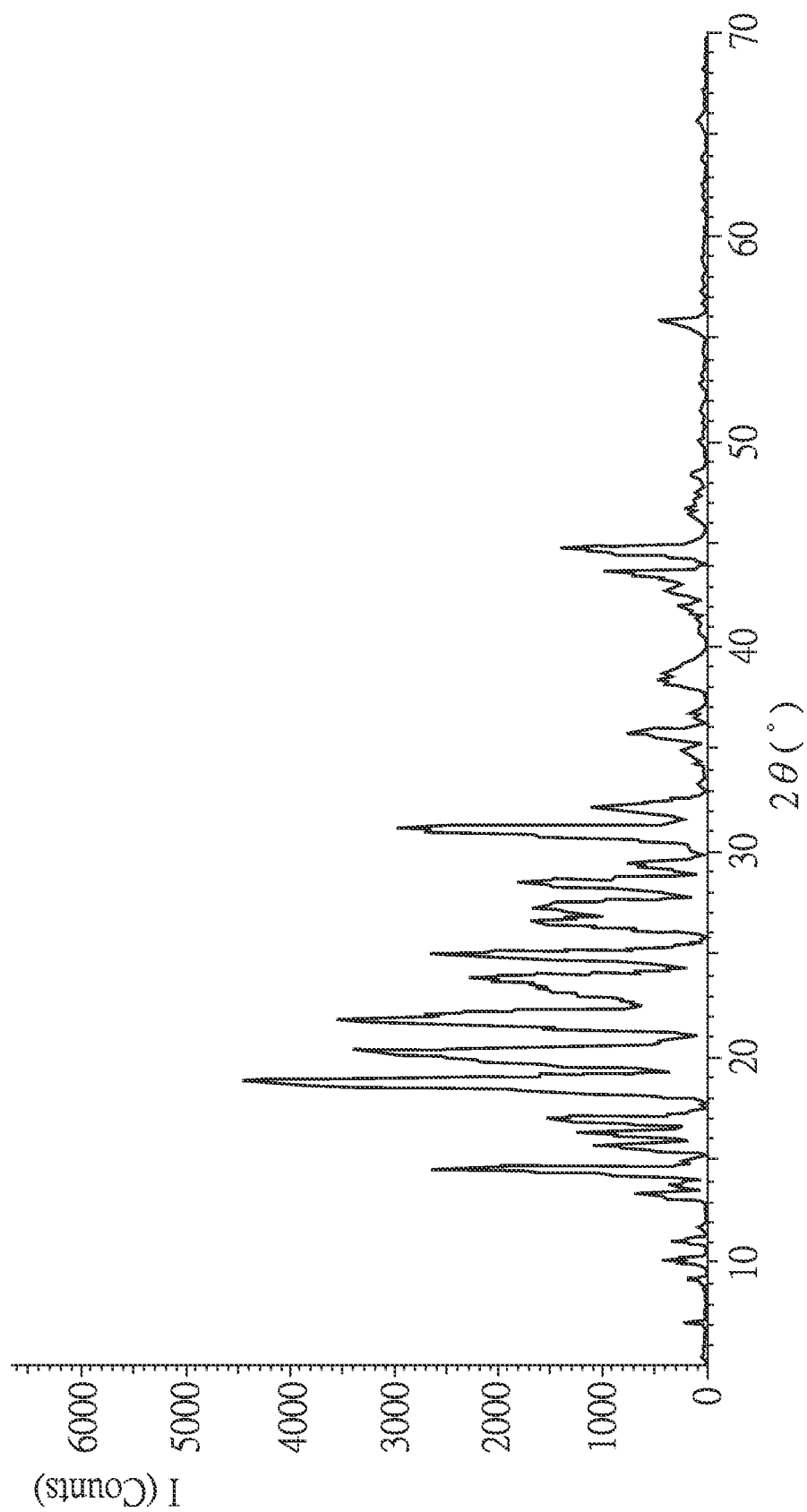
FIG. 6 shows an XRD pattern of a crystalline form of a compound of formula (2) according to Example 13 of the present disclosure.

In the aforesaid embodiment, the XRD pattern of the crystalline form of the compound of formula (2) may be substantially as depicted in FIG. 5 or FIG. 6.

In the aforesaid embodiments, the crystalline form of the compound of formula (2) may have a DSC curve having a melting endotherm peak at about 168-170° C. In addition, the crystalline form of the compound of formula (2) may have the DSC curve further having another melting endotherm peak at about 85-95° C.

The present disclosure also provides a process for preparing the aforesaid crystalline form of the compound of formula (2), comprising the following steps: crystallizing the compound of formula (2) in a solvent to obtain the aforesaid crystalline form of the compound of formula (2). The crystalline form of the compound of formula (2) can be obtained by recrystallized (S)-3-(4-((2-methyl-1-(4-(5-phenyl-1,3,4-oxadiazol-2-yl)phenyl)propyl)amino)benzamido)propanoic acid in a suitable solvent. Examples of the solvent may include, but are not limited to, methanol, ethanol, isopropanol, 1-butanol, tert-butanol, ethyl acetate, butyl acetate, acetone, acetonitrile, dicholoromethane or a combination thereof. Herein, if two or more solvents are used, the compound of formula (2) can be dissolved into a mixture of two or more solvents, or the compound of formula (2) can be dissolved into one solvent to form a mixture, followed by sequentially adding other solvents into the mixture. In addition, the compound of formula (2) can be crystallized at a temperature ranging from 0° C. to 40° C. for 2 hr to 12 hr, for example, from 15° C. to 25° C. Furthermore, a heating step may be selectively performed before the compound of formula (2) is crystallized to facilitate the dissolution of the compound of formula (2), The temperature of the heating step may be, for example, the reflux temperature.

The present disclosure provides a salt form of the compound of formula (2).

In one embodiment, the XRD pattern of the salt form of the compound of formula (2) may be substantially as depicted in any of FIG. 7 to FIG. 10.

In the aforesaid embodiment, the salt form of the compound of formula (2) may be a metal salt of group IA or group IIA.

In the aforesaid embodiments, the salt form of the compound of formula (2) may be a sodium salt, a potassium salt, a magnesium salt or a calcium salt.

The present disclosure provides an amorphous form of the compound of formula (1) or formula (2).

Figure 11:
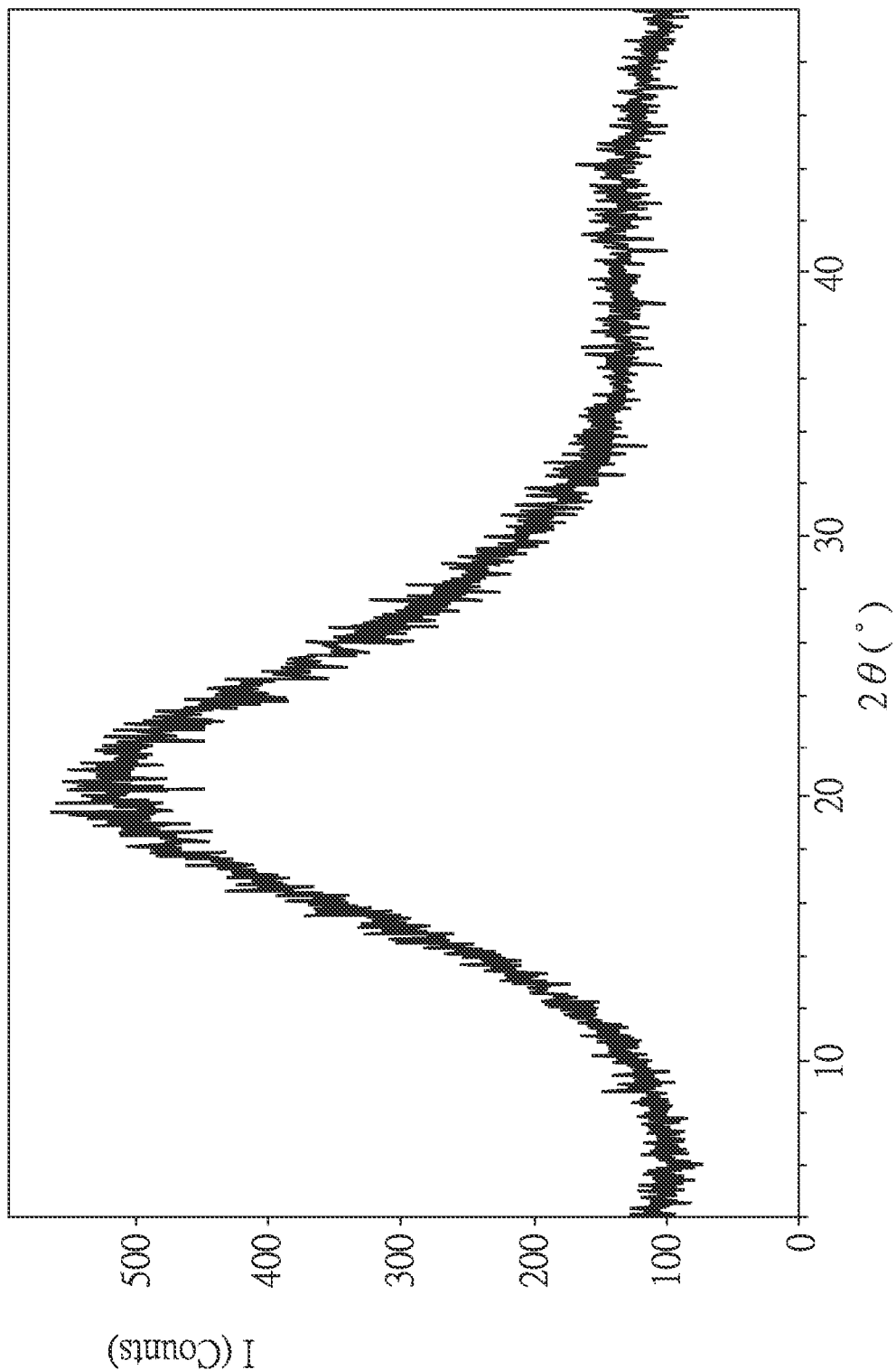
FIG. 11 shows an XRD pattern of an amorphous form of a compound of formula (1) according to Example 18 of the present disclosure.

In one embodiment, the XRD pattern of the amorphous form of the compound of formula (1) may be substantially as depicted in FIG. 11.

The present disclosure also provides a use of any of the crystalline form of the compound of formula (1) or formula (2), the amorphous form of the compound of formula (1) or formula (2) or the salt of the compound of formula (2) described above for reducing the glycemic level in a subject or treating disorders associated with glucagon.

The present disclosure also provides a pharmaceutical composition for reducing the glycemic level in a subject or treating disorders associated with glucagon, which may comprises: the crystalline form of the compound of formula (1) or formula (2), the amorphous form of the compound of formula (1) or formula (2) or the salt of the compound of formula (2) described above; and a pharmaceutically acceptable carrier, excipient or diluent.

The present disclosure also provides use of the aforesaid pharmaceutical composition for reducing the glycemic level in a subject or treating disorders associated with glucagon.

The present disclosure further provides a method for reducing the glycemic level in a subject or treating disorders associated with glucagon, which may comprises: administering to a subject in need thereof an effective amount of the crystalline form of the compound of formula (1) or formula (2), the amorphous form of the compound of formula (1) or formula (2) or the salt of the compound of formula (2) described above, or the pharmaceutical composition comprising the same.

In the present disclosure, the aforesaid subject may be mammal, for example, a human, a pig, a horse, a cow, a dog, a cat, a mouse or a rat.

In the present disclosure, the diseases, conditions or disorders associated with glucagon can be, for example, hyperglycemia, Type II diabetes, metabolic syndrome, impaired glucose tolerance, glucosuria, diabetic nephropathy, diabetic neuropathy, diabetic retinopathy, hyperinsulinemia, insulin resistance syndrome, cataracts, obesity, dyslididemia, hypertension and myocardial infarction. However, the present disclosure is not limited thereto, and the pharmaceutical composition of the present disclosure can be applied to any other diseases, conditions or disorders associated with the glucagon signaling pathway. In one aspect of the present disclosure, the diseases, conditions or disorders associated with glucagon may be hyperglycemia, Type II diabetes, impaired glucose tolerance, insulin resistance syndrome or obesity. In another aspect of the present disclosure, the diseases, conditions or disorders associated with glucagon may be Type II diabetes.

The present disclosure also provides novel compounds of formula (3) or salts thereof,

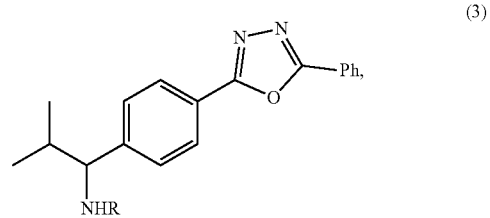

(3)

wherein R is H, $C_{1-6}$ alkyl being optionally substituted with phenyl, $C_{2-6}$ alkenyl, —S(=O)$R_1$, —P(=O)$R_2R_3$ or phenyl substituted with —COO$R_4$; wherein $R_1$ is $C_{1-6}$ alkyl, $R_2$ is aryl, $R_3$ is aryl, and $R_4$ is H or $C_{1-6}$ alkyl.

In one embodiment, compounds of formula (3) each have R being H, benzyl, allyl, —S(=O)$R_1$, —P(=O)$R_2R_3$ or phenyl substituted with —COO$R_4$; wherein $R_1$ is propyl, $R_2$ is phenyl, $R_3$ is phenyl, and $R_4$ is H or ethyl. In this embodiment, an exemplary compound of formula (3) has R being H.

In the aforesaid embodiment, compounds of formula (3) each may be represented by the following formula (3'),

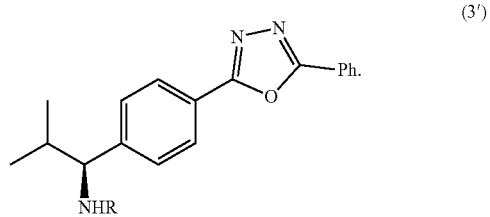

(3')

In this embodiment, an exemplary compound of formula (3) is represented by the following formula (3-1),

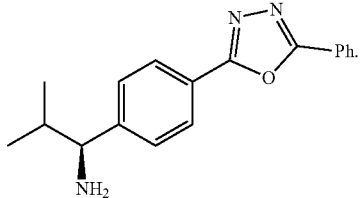
(3-1)

The present disclosure also provides a method for preparing the above compound of formula (3-1), comprising the following steps: reacting methyl 4-formylbenzoate to form the compound of formula (3-1).

In one embodiment, the step of reacting methyl 4-formylbenzoate to form the compound of formula (3-1) may comprise the following steps:
reacting methyl 4-formylbenzoate to form a compound of formula (A);

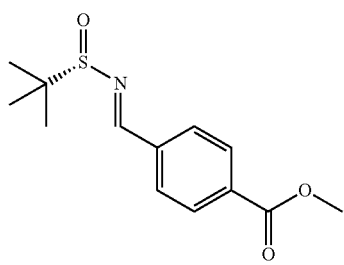
(A)

reacting the compound of formula (A) to form a compound of formula (B);

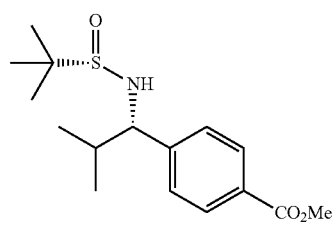
(B)

reacting the compound of formula (B) to form a compound of formula (C);

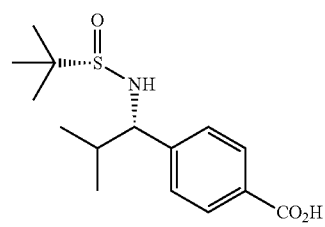
(C)

reacting the compound of formula (C) to form a compound of formula (D);

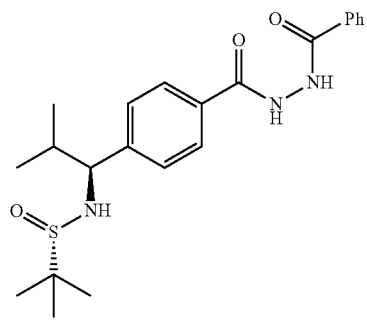
(D)

reacting the compound of formula (D) to form a compound of formula (E); and

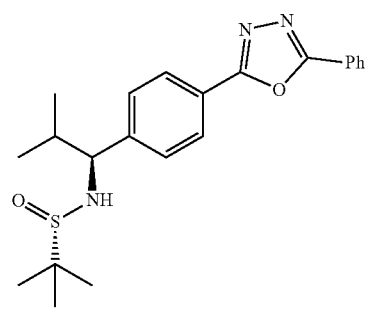
(E)

reacting the compound of formula (E) to form the compound of the formula (3-1).

In the step of reacting methyl 4-formylbenzoate to form the compound of formula (A), methyl 4-formylbenzoate may be reacted with (S)-2-methylpropane-2-sulfinamide to obtain the compound of formula (A) by using $Cs_2CO_3$. Alternatively, methyl 4-formylbenzoate may be reacted with (S)-2-methylpropane-2-sulfinamide to obtain the compound of formula (A) by using titanium tetraisopropoxide; and in this case, a compound of formula (A') may be further formed together with the compound of formula (A),

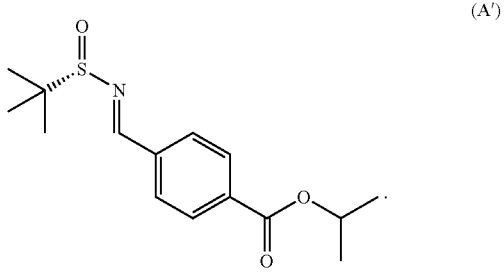 [SMILES: CC(C)OC(=O)c1ccc(/C=N/[S@@](=O)C(C)(C)C)cc1]
(A')

In the step of reacting the compound of formula (A) to form the compound of formula (B), the compound of formula (A) may be reacted with isopropylmagnesium chloride to obtain the compound of formula (B). In the case when the compound of formula (A') is formed together with the compound of formula (A), a compound of formula (B') may also be further formed together with the compound of formula (B),

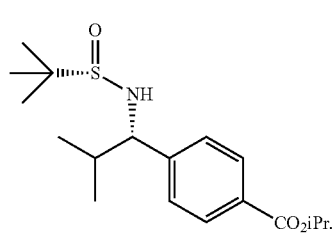

(B')

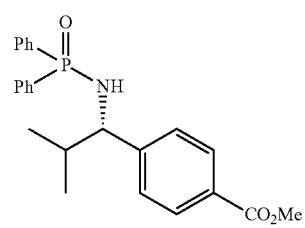

(H)

reacting the compound of formula to form a compound of formula (I);

In the step of reacting the compound of formula (B) to form the compound of formula (C), the compound of formula (B) may be converted into the compound of formula C by using a base such as LiOH, NaOH or KOH. In the case when the compound of formula (B') is formed together with the compound of formula (B), the compound of formula (B') may also be converted into the compound of formula (C) by using the aforesaid base.

Herein, the compound of formula (C) may be recrystallized by using a suitable solvent. Examples of the suitable solvent may comprise, but are not limited to, acetone, ethyl acetate, methanol, ethanol, Cert-butyl methyl ether (TBME), ether or a combination thereof.

In the step of reacting the compound of formula (C) to form the compound of formula (D), the compound of formula (C) may be reacted with benzohydrazide to form the compound of formula (D).

In the step of reacting the compound of formula (D) to form the compound of formula (E), the cyclolization reaction may be performed in the presence of para-toluenesulfonyl chloride and triethylamine.

In the step of reacting the compound of formula (E) to form the compound of the formula, (3-1), the sulfinyl group of the compound of formula (E) may be removed by using an acid, for example, HCl.

In another embodiment, the step of reacting methyl 4-formylbenzoate to form the compound of formula (3-1) may comprise the following steps:

reacting methyl 4-formylbenzoate to form a compound of formula (G);

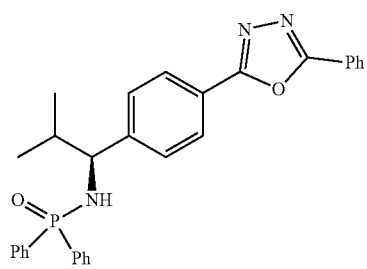

(I)

reacting the compound of formula (I) to form a compound of formula (J);

(J)

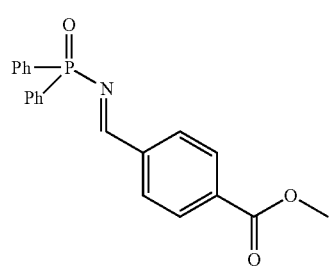

reacting the compound of formula (J) to form a compound of formula (K); and (K)

(G)

reacting the compound of formula (K) to form the compound of formula (3-1).

In the step of reacting methyl 4-formylbenzoate to form the compound of formula (G), methyl 4-formylbenzoate may be reacted with diphenylphosphinic amide to form the compound of formula (G).

In the step of the compound of formula (G) to form the compound of formula (H), the compound of formula (G)

reacting the compound of formula (G) to form a compound of formula (H);

may be reacted with isopropylmagnesium chloride to form the compound of formula (H).

In the step of reacting the compound of formula (H) to form the compound of formula (I), the compound of formula (H) may be converted into the compound of formula (I) by using a base such as LiOH, NaOH or KOH.

In the step of reacting the compound of formula (I) to form the compound of formula (J), the compound of formula (I) may be reacted with benzohydrazide to obtain the compound of formula (J).

In the step of reacting the compound of formula (J) to form the compound of formula (K), the cyclolization reaction may be performed in the presence of p-toluenesulfonyl chloride and triethylamine.

In the step of reacting the compound of formula (K) to form the compound of formula (3-1), the phosphinic group may be removed by using an acid, for example, HCl.

In another embodiment, the step of reacting methyl 4-formylbenzoate to form the compound of formula (3-1) may comprise the following steps:

reacting methyl 4-formylbenzoate to form a compound of formula (L);

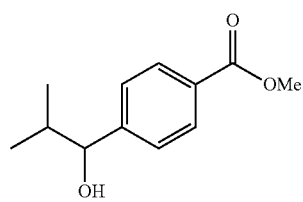
(L)

reacting the compound of formula (L) to form a compound of formula (M);

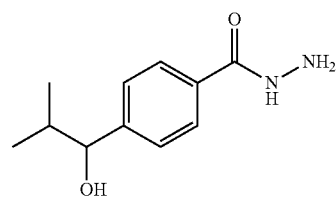
(M)

reacting the compound of formula (M) to form a compound of formula (O);

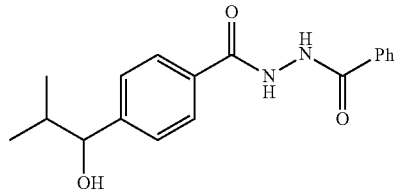
(O)

reacting the compound of formula (O) to form a compound of formula (P); and

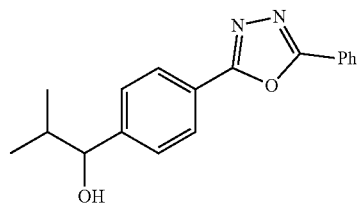
(P)

reacting the compound of formula a (P) to form the compound of formula (3-1).

In the step of reacting methyl 4-formylbenzoate to form the compound of formula (L), methyl 4-formylbenzoate may be reacted with isopropylmagnesium chloride to form the compound of formula (L).

In the step of reacting the compound of formula (L) to form the compound of formula (M), the compound of formula (L) may be reacted with hydrazine to form the compound of formula (M).

In the step of reacting the compound of formula (M) to form the compound of formula (O), the compound of formula (M) may be reacted with benzoic acid to form the compound of formula (O).

In the step of reacting the compound of formula (O) to form the compound of formula (P), the cyclolization reaction may be performed in the presence of p-toluenesulfonyl chloride.

In one aspect, the step of reacting the compound of formula (P) to form the compound of formula (3-1) may comprise the following steps:

reacting the compound of formula (P) to form a compound of formula (P1),

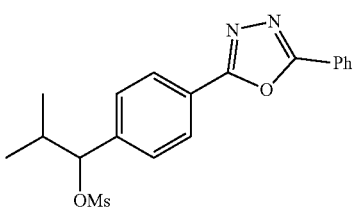
(P1)

reacting the compound of formula (P1) to form a compound of formula (P2); and

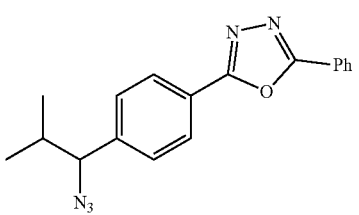
(P2)

reacting the compound of formula (P2) to form the compound of formula (3-1).

In the step of reacting the compound of formula (P) to form the compound of formula (P1), the compound of formula (P) may be reacted with methanesulfonyl chloride to form the compound of formula (P1).

In the step of reacting the compound of formula (P1) to form the compound of formula (P2), the compound of formula (P1) may be reacted with sodium azide to form the compound of formula (P2).

In the step of reacting the compound of formula (P2) to form the compound of formula (3-1), the compound of formula (P2) may be converted into the compound of formula (3-1) under Staudinger reaction.

In another aspect, the step of reacting the compound of formula (P) to form the compound of formula (3-1) may comprise the following steps:

reacting the compound of formula (P) to form a compound of formula (P3),

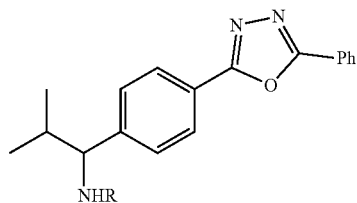

(P3)

wherein R is benzyl or allyl; and reacting the compound of formula (P3) to form the compound of formula (3-1).

In the step of reacting the compound of formula (P) to form the compound of formula (P3), the compound of formula (P) may be reacted with allylic amine or benzylic amine to form the compound of formula (P3).

In the step of reacting the compound of formula (P3) to form the compound of formula (3-1), the compound of formula (P3) may be converted into the compound of formula (3-1) by hydrogenolysis.

The present disclosure also provides a method for preparing the above compound of formula (1), comprising the following steps: reacting the above compound of formula (3-1) to form the compound of formula (1).

In one aspect, the compound of formula (3-1) may be directly converted into the compound of formula (1). In this case, the compound of formula (3-1) may be reacted with ethyl 3-(4-halobenzamido) propanoate to obtain the compound of formula (1).

In one embodiment, ethyl 3-(4-halobenzamido) propanoate may be ethyl 3-(4-bromobenzamido) propanoate or ethyl 3-(4-iodobenzamido) propanoate.

In the aforesaid embodiment, the compound of formula (3-1) may be reacted with ethyl 3-(4-halobenzamido) propanoate by using a ligand and a base.

In the aforesaid embodiments, the ligand may be 2,2'-bis (diphenylphosphino)-1,1'-binaphthyl (BINAP) or 2-Dicyclohexylphosphino-2',4',6'-triisopropylbiphenyl (XPhos).

In the aforesaid embodiments, the base may be $Cs_2CO_3$.

In the aforesaid embodiments, the compound of formula (3-1) may be reacted with ethyl 3-(4-halobenzamido) propanoate at a reflux temperature.

In another embodiment, the step of reacting the compound of formula (3-1) to form the compound of formula (I) may comprise the following steps:

reacting the compound of formula (3-1) to form a compound of formula (U);

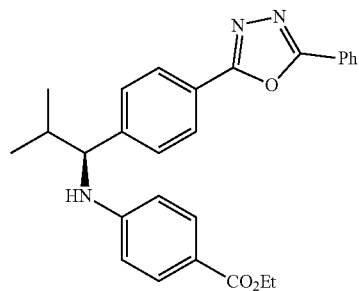

(U)

converting the compound of formula (U) into a compound of formula (V); and

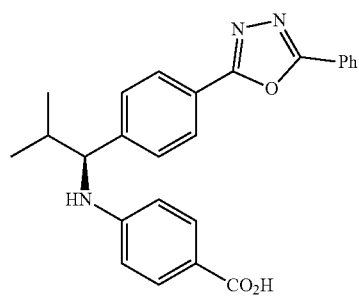

(V)

reacting the compound of formula (V) to form the compound of formula (1).

In the step of reacting the compound of formula (3-1) to form the compound of formula (U), the compound of formula (3-1) may be reacted with ethyl 4-(((trifluoromethyl)sulfonyl)oxy) benzoate or ethyl 4-halobenzoate to form the compound of formula (U). Examples of the ethyl 4-halobenzoate may be ethyl 4-bromobenzoate or ethyl 4-iodobenzoate.

In one embodiment, the compound of formula (3-1) may be reacted with ethyl 4-(((trifluoromethyl)sulfonyl)oxy) benzoate or ethyl 4-halobenzoate at a reflux temperature.

In the aforesaid embodiment, the compound of formula (3-1) may be reacted with ethyl 4-(((trifluoromethyl)sulfonyl)oxy) benzoate or ethyl 4-halobenzoate by using a ligand and a base.

In the aforesaid embodiments, the ligand may be BIANP, XPhos, 2-Dicyclohexylphosphino-2',6'-dimethoxybiphenyl (SPhos) or (2-Biphenyl)dicyclohexylphosphine (CyJohnPhos).

In the aforesaid embodiments, the base may be $Cs_2CO_3$.

In the step of converting the compound of formula (U) into the compound of formula (V), the compound of formula (U) may converted to the compound of formula (V) by using a base such as LiOH, NaOH or KOH.

In the step of reacting the compound of formula (V) to form the compound of formula (1), the compound of formula (V) may be reacted with ethyl 3-aminopropanoate hydrochloride to form the compound of formula (1).

In one embodiment, the compound (V) may be reacted with ethyl 3-aminopropanoate hydrochloride by using a coupling agent to form the compound of formula (1).

In the aforesaid embodiment, the coupling agent may be 1-ethyl-3-(3-dimethylaminopropyl)carbodiimide (EDCI, hydroxybenzotriazole (HOBO, 2-(1H-benzotriazol-1-yl)-1, 1,3,3-tetramethyluronium hexafluorophosphate (HBTU), 1-[Bis(dimethylamino)methylene]-1H-1,2,3-triazolo[4,5-b]pyridinium 3-oxide hexafluorophosphate (HAITI), 2-chloro-4,6-dimethoxy-1,3,5-triazine (CDMT), enzotriazol-1-yloxytripyrrolidinophosphonium hexafluorophosphate (PyBOP) or a combination thereof.

The present disclosure also provides another method for preparing the above compound of formula (1), comprising the following steps:
reacting methyl 4-formylbenzoate to form the above compound of formula (L);
reacting the compound of formula (L) to form the above compound of formula (M);
reacting the compound of formula (M) to form the compound of formula (O);
reacting the compound of formula (O) to form the compound of formula (P);
reacting the compound of formula (P) to form a compound of formula (Q);

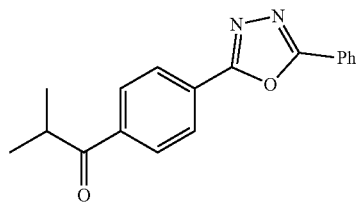

(Q)

reacting the compound of formula (Q) to form a compound of formula (R);

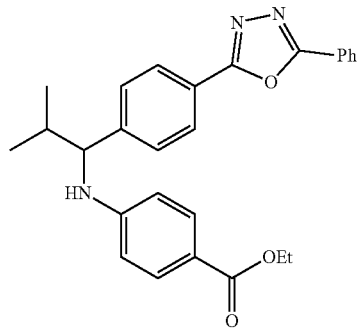

(R)

reacting the compound of formula (R) to form a compound of formula (S);

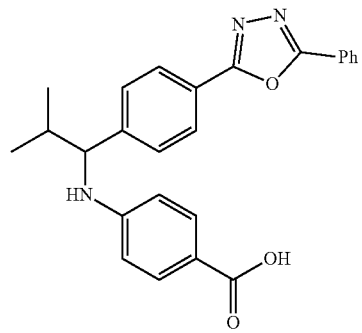

(S)

reacting the compound of formula (S) to form the above compound of formula (V); and reacting the compound of formula (V) to form the compound of formula (I).

Herein, the steps for forming the compounds of formula (L), (M), (O) and (P) are similar to those illustrated before, and are not repeated again. In addition, the step for forming the compound of formula (1) from the compound of formula (V) is also similar to that illustrated before, and is not repeated again.

In the step of reacting the compound of formula (P) to form the compound of formula (Q), the compound of formula (P) is reacted with pyridinium chlorochromate to form the compound of formula (Q).

In the step of reacting the compound of formula (Q) to form the compound of formula (R), the compound of formula (Q) is reacted with ethyl 4-aminobenzoate to form the compound of formula (R).

In the step of reacting the compound of formula (R) to form the compound of formula (S), the compound of formula (R) is converted into the compound of formula (S) by using a base such as LiOH, NaOH or KOH.

In the step of reacting the compound of formula (S) to form the compound of formula (V), the compound of formula (S) is converted into the compound of formula (V) with a chiral amine or a chiral acid. Examples of the chiral amine may include, but are not limited to, (R)-phenethylamine. Examples of the chiral acid may include, but are not limited to, (1R)-(−)-10-camphorsulfonic acid.

The present disclosure further provides another method for preparing the above compound of formula (2), comprising the following steps: converting the compound of formula (1) into the compound of formula (2).

In one embodiment, the compound of formula (1) may be converted into the compound of formula (2) by using a base.

In the aforesaid embodiment, the base may be LiOH, NaOH or KOH.

The following embodiments are made to clearly exhibit the above-mentioned and other technical contents, features and/or effects of the present disclosure. Through the exposition by means of the specific embodiments, people would further understand the technical means and effects the present disclosure adopts to achieve the above-indicated objectives. Moreover, as the contents disclosed herein should be readily understood and can be implemented by a person skilled in the art, all equivalent changes or modifications which do not depart from the concept of the present disclosure should be encompassed by the appended claims.

Moreover, in the present specification, a value may be interpreted to cover a range within ±10% of the value, and in particular, a range within ±5% of the value, except otherwise specified; a range may be interpreted to be composed of a plurality of subranges defined by a smaller endpoint, a smaller quartile, a median, a greater quartile, and a greater endpoint, except otherwise specified.

EXAMPLE

Without further elaboration; it is believed that one skilled in the art can, based on the above description, utilize the present disclosure to its fullest extent. The following specific examples are therefore to be construed as merely illustrative, and not limitative of the remainder of the disclosure in any way whatsoever. All publications cited herein are incorporated by reference in their entirety.

Unless otherwise stated, all starting materials used were commercially available and used as supplied. Reactions requiring anhydrous conditions were performed in flamedried glassware and cooled under an argon or nitrogen atmosphere. Unless otherwise stated, reactions were carried out under argon or nitrogen and monitored by analytical thin-layer chromatography, performed on glass-backed plates (5 cm_10 cm) precoated with silica gel 60 F254 as supplied by Merck. Visualization of the resulting chromatograms was done by looking under an ultraviolet lamp (λ=254 nm), followed by dipping in an nBuOH solution of Ninhydrin (0.3% w/v) containing acetic acid (3% v/v) or ethanol solution of phosphomolybdic acid (2.5% w/v) and charring by heat gun. Solvents for reactions were dried under an argon or nitrogen atmosphere prior to use as follows: THF, Toluene, and DCM were dried by the column of Dried molecular Sieve 5A (LC technology solution Inc). and DMF from calcium hydride or anhydrous with commercial available. Flash chromatography was used routinely for purification and separation of product mixtures using RediSep Rf Silica Gel Disposable Flash Columns, Gold® 20-40/40-60 microns silica gel and Reusable Redi Sep Rf Gold® C18 Reversed Phase columns, 20-40 microns supplied by Redi Sep. Eluent systems are given in volume/volume concentrations. 13C and 1H NMR spectra were recorded on Bruker AVIII (400 MHz). Chloroform-d or dimethyl sulfoxide-d6 and $CD_3OD$ was used as the solvent and TMS (δ 0.00 ppm) as an internal standard. Chemical shift values are reported in ppm relative to the TMS in delta (δ) units. Multiplicities are recorded as s (singlet), br s (broad singlet), d (doublet), t (triplet), q (quartet), dd (doublet of doublet), dt (doublet of triplet), m (multiplet). Coupling constants (J) are expressed in Hz. Electrospray mass spectra (ISMS) were recorded using a Thermo LTQ XL mass spectrometer. Spectral data were recorded as m/z values.

Example 1—Preparation of Compound of Formula (1) or (2)

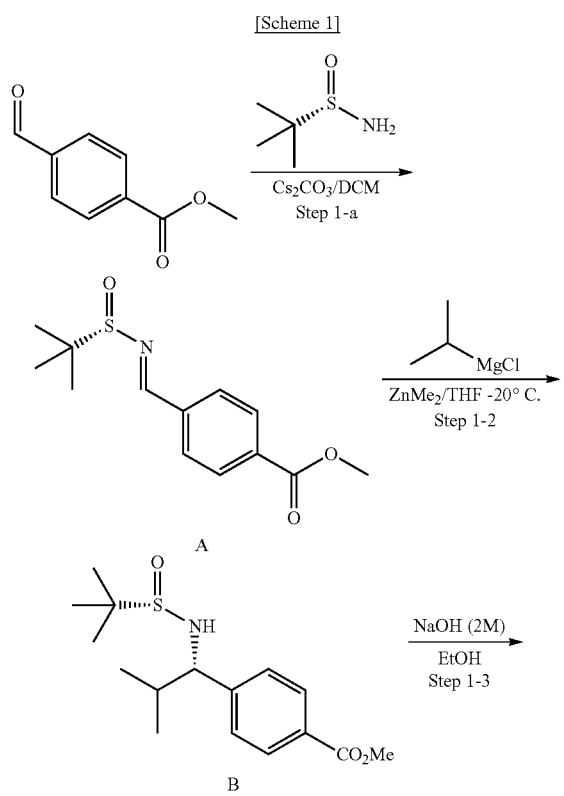

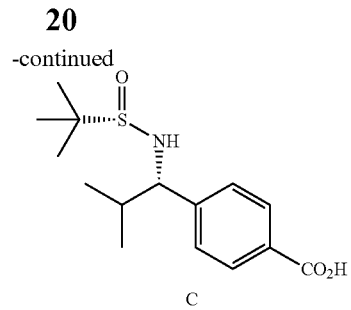

Step 1-a: Preparation of Methyl (S,E)-4-(((tert-butylsulfinyl)imino)methyl)benzoate (A)

To a solution of Methyl 4-formylbenzoate (500 g) in DCM (10 L) under $N_2$ atmosphere at 15-35° C. (S)-2-methylpropane-2-sulfinamide (443 g, 3 mol) was added, then $Cs_2CO_3$ (1172 g) was added finally. The mixture was stirred for 16 h. The reaction was filtered and the filtrate was dried by vapor and afforded Compound A (720 g, 89%) as a white solid. $^1$H-NMR ($CDCl_3$, 400 MHz): δ 8.63 (s, 1H), 8.13 (d, J=8.8 Hz, 2H), 7.91 (d, J=8.8 Hz, 2H), 3.95 (s, 3H), 1.28 (s, 9H).

Step 1-2: Preparation of Methyl 4-((S)-1-(((S)-tert-butylsulfinyl)amino)-2-methylpropyl) benzoate (B)

To a solution of Compound A (106.8 g, 0.4 mol) in THF (954 mL) under $N_2$ atmosphere at −25~−20° C. $ZnMe_2$ Toluene solution (1.2 M, 50 mL) was added within 20 mins at −25~−20° C. Then the reaction was kept to stir for another 10 mins at −25~−20° C. Isopropylmagnesium chloride THF solution (2M, 240 mL) was added within 30 mins and keep the temperature was below −20° C. The mixture was stirred for another 1.5 h at 25~−20° C. The reaction was quenched with MeOH (25 mL) within 10 mins at −20° C. Then sat. $NH_4Cl_{(aq)}$ (25 mL) was added at −10~0° C. The reaction temperature was returned to 15-25° C. for one hour, then mixture was filtered and the filtrate was dried by vapor and afforded Compound B (124 g, 100%) as a Colorless oil. $^1$H-NMR ($CDCl_3$, 400 MHz): δ 8.00 (d, J=8.8 Hz, 2H), 7.91 (d, J=8.8 Hz, 2H), 4.18 (t, J=6.4 Hz, 1H), 3.90 (s, 3H), 3.47 (d, J=6.4 Hz, 1H), 2.24-2.17 (m, 1H), 1.23 (s, 9H), 0.93 (d, J=6.9 Hz, 3H), 0.80 (d, J=6.9 Hz, 3H). MS (M+1): 312.

Step 1-3: Preparation of 4-((S)-1-(((S)-tert-butylsulfinyl)amino-2-methylpropyl)benzoic acid (C)

To a solution of Compound B (12.4 g, 0.4 mol) in EtOH (790 mL) at 20-30° C., NaOH (40 g) in DI water (500 g) was added into the solution. The mixture was stirred for 16 h at 20-30° C. or at 80-85° C. for 2 h. Then the reaction solvent was distilled at 85-90° C. about 650 mL. The reaction was neutralized with $HCl_{(aq)}$ (4N, 300-400 mL) at 4-6° C. until pH=4-5 and the required solid was formed. The solid was filtered and washed with DI water (1000 g). The solid was stirred in Acetone (300 mL) and MeOH (30 mL) for 30 min at 25-30° C. and then filtered and afforded Compound C (83 g, 70%) as a white solid. $^1$H-NMR ($CDCl_3$, 400 MHz): δ 7.72 (d, J=8.8 Hz, 2H), 7.25 (d, J=8.8 Hz, 2H), 4.39 (d, J=6.8 Hz, 1H), 4.01 (t, J=6.8 Hz, 1H), 2.14-2.09 (m, 1H), 1.33 (s, 9H), 1.03 (d, J=6.9 Hz, 3H), 0.74 (d, J=6.9 Hz, 3H), MS (M+1): 298.

In addition, different recrystallization conditions were also examined herein, and the results are shown in the following Table 1.

TABLE 1

Different recrystallization conditions used in Step 1-3

| Solvent A | Solvent B | T (° C.) | Yield (%) | d.e. (%) |
|---|---|---|---|---|
| Acetone | MeOH | 25-30 | 70 | >99.5 |
| Acetone | TBME | 25-30 | 90 | 90 |
| Acetone | Ether | 25-30 | 95 | 85 |
| Acetone | EtOH | 25-30 | 50 | >99.5 |
| Acetone | — | 25-30 | 80 | 95 |
| EtOAc | MeOH | 25-30 | 65 | 95 |
| — | MeOH | 25-30 | 30 | >99 |

[Scheme 2]

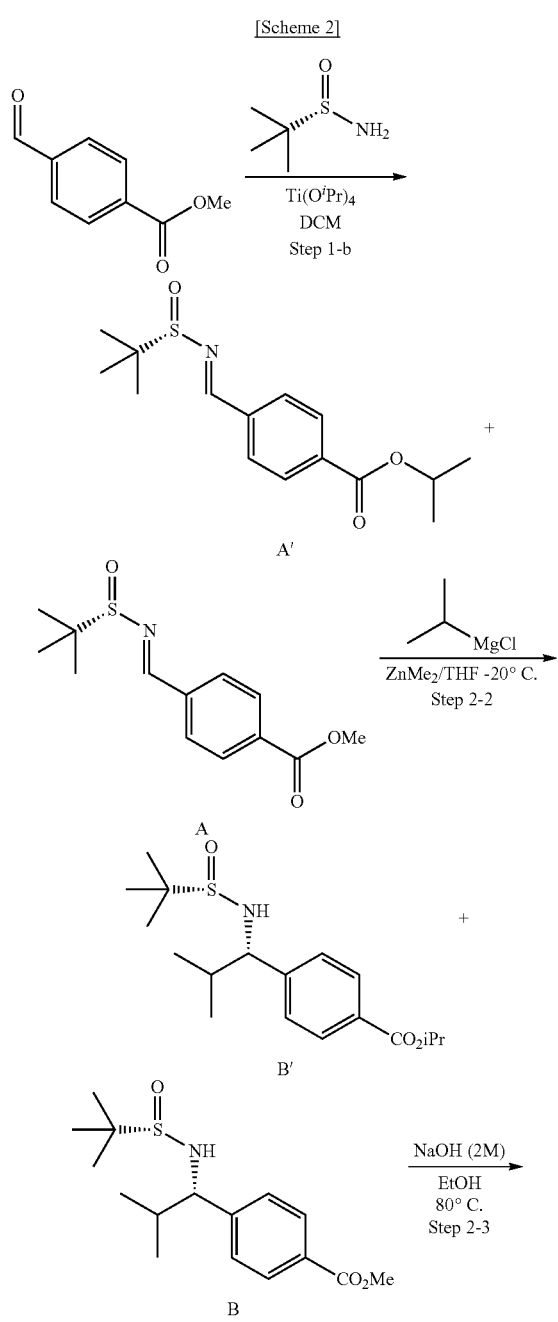

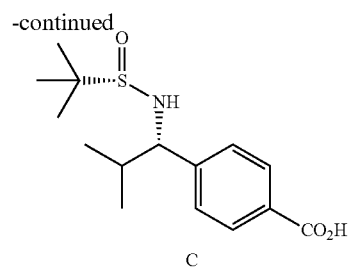

Step 1-b: Preparation of Isopropyl (S,E)-4-(((tert-butylsulfinyl)imino)methyl)benzoate (A')

To a solution of Methyl 4-formylbenzoate (50 g) in DCM (660 g) at 15-25° C., (S)-2-methylpropane-2-sulfinamide (44.4 g) was added, purge the $N_2$ for 3 times, TTIP (173.00 g) was added slowly to the mixture under $N_2$ protection. The mixture was stirred for 16 h at 20-25° C. Cooling the temperature to 5-10° C., 20% $Na_2CO_{3(aq)}$ (150 g) and water (100 g) was added into the mixture to stop the reaction, the crude mixture was extracted with additional DCM (396 g). Removed the aqueous layer and the organic layer was extracted with brine (200 g), then remove the brine layer, anhydrous $Na_2SO_4$ (25.0) g) was added to the organic layer and then the mixture was filtered and the filtrate was dried by vapor and afforded Compound A' and Compound A (85:15, 81.46 g, 91%) as a white solid. $^1$H-NMR (CDCl$_3$, 400 MHz): δ 8.63 (s, 1H), 8.11 (d, J=8.8 Hz, 2H), 7.89 (d, J=8.8 Hz, 2H), 3.92 (m, 1H), 1.28 (s, 9H), 1.25 (d, J=6.9 Hz, 6H).

Step 2-2: Preparation of Isopropyl 4-((S)-(1)-(((S)-tert-butylsulfinyl)amino)-2-methylpropyl) benzoate (B')

To a solution of Compound A' mixing with Compound A (81.46 g) in THF (555 g) under $N_2$ atmosphere at −25~−20° C., ZnMe$_2$ Toluene solution (1 M, 39.1 g) was added within 20 mins at −25~−20° C. Then the reaction was kept to stir for another 10 mins at −25~−20° C. Isopropylmagnesium chloride THF solution (2M, 175.1 g) was added within 30 mins, and keep the temperature was below −2.0° C. The mixture was stirred for another 1.5 h at 25~−20° C. The reaction was quenched with MeOH (21.1 g) within 10 mins at −20° C. Then sat. $NH_4Cl_{(aq)}$ (21.1 g) was added at −10~0° C. The reaction temperature was returned to 15-25° C. for one hour, then mixture was filtered and the filtrate was dried by vapor and afforded Compound. B' and Compound B (85:15, 101.1 g, 100%) as a Colorless oil. $^1$H-NMR, (CDCl$_3$, 400 MHz): δ 8.00 (d, J=8.8 Hz, 2H); 7.91 (d, J=8.8 Hz, 2H), 4.18 (t, J=6.4 Hz, 1H), 3.90 (s, 3H), 3.47 (d, J=6.4 Hz, 1H), 2.24-2.17 (m, 1H), 1.23 (s, 9H), 0.93 (d, J=6.9 Hz, 3H), 0.80 (d, J=6.9 Hz, 3H). MS (M+1): 340.

Step 2-3: Preparation of 4-((S)-1-(((S)-tert-butylsulfinyl)amino-2-methylpropyl)-benzoic acid (C)

To a solution of Compound B' mixing with Compound B (101.1 g) in EtOH (210 g) at 20-30° C., NaOH (61 g) in DI water (313 g) was added into the solution. The mixture was stirred for 1.5 h at 70-75° C. Then the reaction solvent was distilled at 85-90° C. about 650 mL. The reaction was neutralized with $HCl_{(aq)}$ (4N, 550-600 mL) at 0-15° C. until pH=1-2 and the required solid was formed. The solid was filtered and washed with DI water (300 g). The solid was stirred in Acetone (180 g) and MeOH (16 g) for 30 mins at 25-30° C. and then filtered and afforded C (59.68 g, 66%).

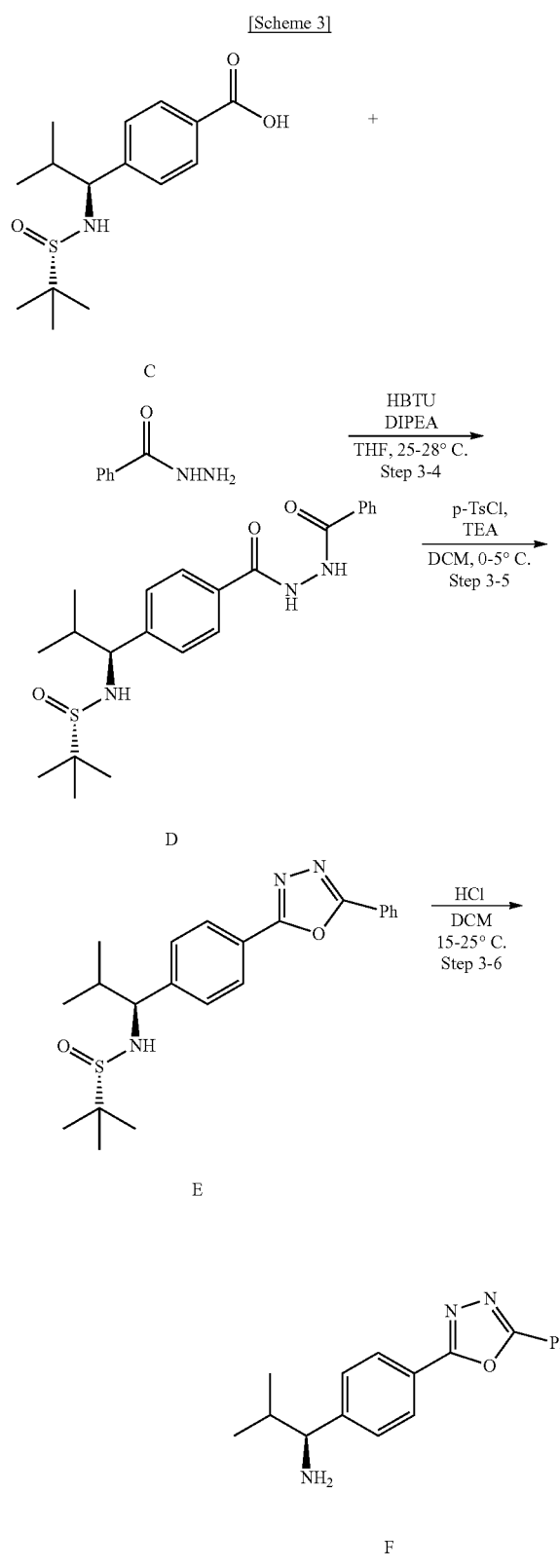

Step 3-4: Preparation of Isopropyl (S)—N—((S)-1-(4-(2-benzoylhydrazine-1-carbonyl)phenyl)-2-methylpropyl)-2-methylpropane-2-sulfinamide (D)

Benzohydrazide (37.4 g) and HBTU (123 g) were dissolved in THF (210 g) at 20-30° C. followed by adding Compound C (74 g, 0.25 mol). DIPEA (96.7 g) was charged in the solution and the mixture was stirred for 16 hours at 25-28° C. The mixture was filtered to remove the unrequired solid and then removed the THF about 900 g by vapor. The crude was added acetonitrile (450 g) to form a suspension solution and then stirred about 2-2.5 h, the solution was filtered to collect the product Compound D (103 g, 100%) as a white solid. $^1$H-NMR (CDCl$_3$, 400 MHz): δ 9.17 (brs, 1H), 7.89 (d, J=7.3 Hz, 2H), 7.77 (d, J=8.3 Hz, 2H), 7.53-7.34 (m, 5H), 4.15 (t, J=6.4 Hz, 1H), 2.24-2.19 (m, 1H), 1.24 (s, 9H), 0.93 (d, J=6.9 Hz, 3H), 0.82 (d, J=6.9 Hz, 3H). MS (M+1): 416.

Step 3-5: Preparation of (S)-2-methyl-N—((S)-2-methyl-1-(4-(5-phenyl-1,3,4-oxadiazol-2-yl) phenyl)propyl)propane-2-sulfinamide (E)

Sulfinamide, Compound (74.9 g) was dissolved in dichloromethane (98.8 g) at 0-5° C. followed by adding para-toluenesulfonyl chloride (41.2 g). Triethylamine (54.7 g) was charged in the solution and the mixture was stirred for 6-8 hours at 0-5° C. 1.2 M NaOH aqueous solution (393 mL) was added at the same temperature and stirred for 1 h. The mixture was extracted with additional dichloromethane (100 g) and brine (150 g). The collected organic layer was added anhydrous Na$_2$SO$_4$ (25.00 g) and then the mixture was filtered and the filtrate was dried by vapor. The residue was dissolved in methyl tert-butyl ether (48.7 g) and Heptanes (44.9 g) was added to form a suspension mixture. The mixture was stirred for 4 h and filtered to collect the product, Compound E (64.8 g, 90%) as a white solid. $^1$H-NMR (CDCl$_3$, 400 MHz): δ 8.15-8.10 (m, 4H), 7.57-7.53 (m, 3H), 7.45 (d, J=8.4 Hz, 2H), 4.22 (t, J=6.3 Hz, 1H), 3.51 (d, J=6.3 Hz, 1H), 2.28-2.21 (m, 1H), 1.26 (s, 9H), 0.98 (d, J=6.9 Hz, 3H), 0.85 (d, J=6.9 Hz, 3H), MS (M+1): 398.

Step 3-6: Preparation of (S)-2-methyl-1-(4-(5-phenyl-1,3,4-oxadiazol-2-yl)phenyl)propan-1-amine (F) (Compound (3-1))

Sulfinamide, Compound E (64.8 g) was dissolved in dichloromethane (98.8 g) at 15-25° C. followed by adding con. HCl (162 g). The mixture was stirred for 4 hours at 25-30° C. The reaction solvent was removed by vapor and purified water (162 g) was added. Cooling the temperature down to 0-5° C. and 4M NaOH aqueous solution (454.1) was added to adjust pH=11-12 at 0-15° C. The precipitated solid was filtered and washed additional purified water (130 g). The precipitated solid was recrystallized with MeOH (40.2 g) under 30-40° C. to form a clean solution and stirred for 4 h at 20-25° C. The solid was filtered again and dried by vacuum to afforded Compound F (40.3 g, 84%) as a white solid, $^1$H-NMR (CDCl$_3$, 400 MHz): δ 8.17-8.08 (m, 4H), 7.58-7.46 (m, 5H), 3.73 (d, J=6.9 Hz, 1H), 1.94-1.86 (m, 1H), 0.99 (d, J=6.9 Hz, 3H), 0.82 (d, J=6.9 Hz, 3H). MS (M+1): 294.

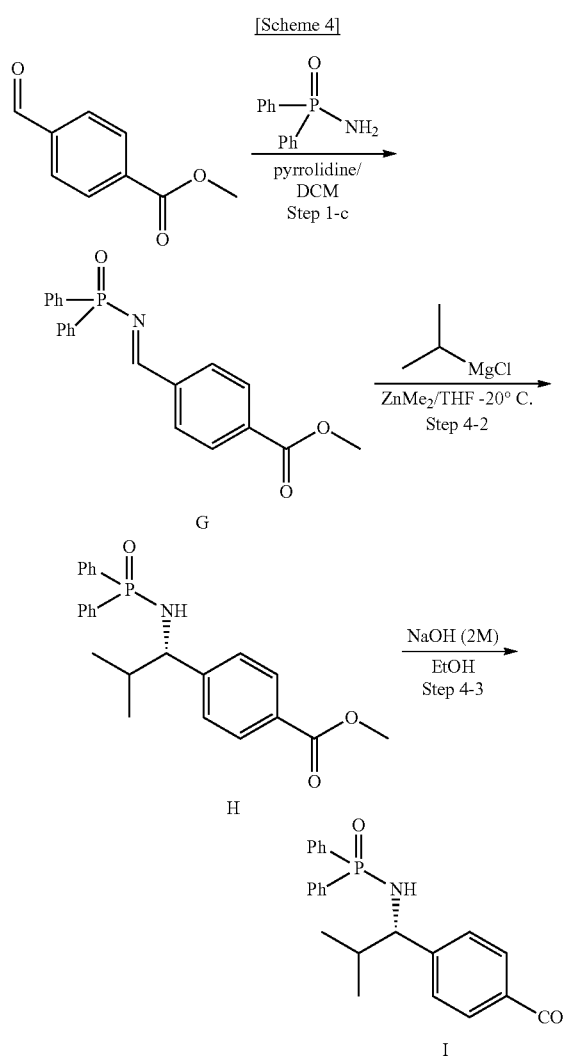

Step 1-c: Preparation of Methyl (E)-4-(((diphenylphosphoryl)imino)methyl)benzoate (G)

To a solution of Methyl 4-formylbenzoate (50 g) in DCM (1 L) under $N_2$ atmosphere at 15-35° C., P,P-diphenylphosphinic amide (66 g, 1 equiv.) and 4 Å MS (250 g) was added, then pyrrolidine (4.3 g, 0.2 equiv.) was added finally. The mixture was stirred at 65° C. for 24 h. Upon cooling to room temperature, the reaction was filtered and the filtrate was dried by vapor. Then the residue was purified by silica gel chromatography to afford Compound C (77 g, 70%) as a white solid.

Step 4-2: Preparation of Methyl (S)-4-(1-(phenylphosphoryl)amino)-2-methylpropyl) benzoate (II)

To a solution of Compound C (144 g) in THF (555 g) under $N_2$ atmosphere at −25~−20° C., ZnMe$_2$ Toluene solution (1 M, 39.1 g) was added within 20 mins at −25~−20° C. Then the reaction was kept to stir for another 10 mins at 25-20° C. Isopropylmagnesium chloride THF solution (2M, 175.1 g) was added within 30 mins, and the temperature was kept below −20° C. The mixture was stirred for another 1.5 h at −25~−20° C. The reaction was quenched with MeOH (21.1 g) within 10 mins at −20° C., Then sat. $NH_4Cl_{(aq)}$ (21.1 g) was added at −10~−0° C. The reaction temperature was returned to 15-25° C. for one hour, then mixture was filtered and the filtrate was dried by vapor to afford Compound H (90:10, 162.8 g, 100%). $^1$H-NMR (CDCl$_3$, 400 MHz): δ 8.35-8.15 (m, 10H), 8.00 (d, J=8.8 Hz, 2H), 7.91 (d, J=8.8 Hz, 2H), 4.18 (t, J=6.4 Hz, 1H), 3.90 (s, 3H), 3.47 (d, J=6.4 Hz, 1H), 2.24-2.17 (m, 1H), 1.23 (s, 9H), 0.93 (d, J=6.9 Hz, 3H), 0.80 (d, J=6.9 Hz, 3H), MS (M+1): 408.

Step 4-3: Preparation of (S)-4-(1-(((diphenylphosphoryl)amino)-2-methylpropyl)benzoic acid (I)

To a solution of Compound H (132 g) in EtOH (210 g) at 20-30° C., NaOH (61 g) in DI water (313 g) was added into the solution. The mixture was stirred for 1.5 h at 70-75° C. Then the reaction solvent was distilled at 85-90° C. about 650 mL. The reaction was neutralized with $HCl_{(aq)}$ (4N, 550-600 mL) at 0-15° C. until pH=1-2 and the required solid was formed. The solid was filtered and washed with DI water (300 g). The solid was stirred in Acetone (180 g) and MeOH (16 g) for 30 mins at 25-30° C. and then filtered to afford Compound I (89.3 g, 70%).

[Scheme 5]

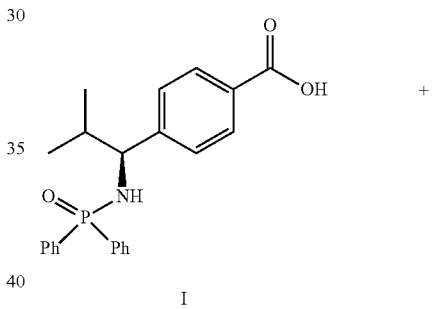

J

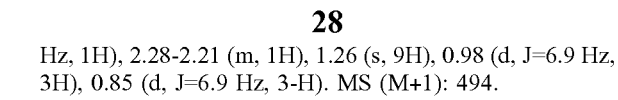

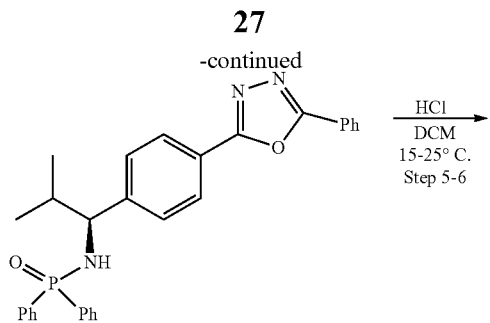

K

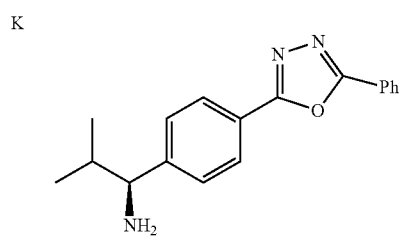

F

Step 5-4: Preparation of (S)—N-(1-(4-(2-benzoyl-hydrazine-1-carbonyl)phenyl)-2-methylpropyl)-P,P-diphenylphosphinic amide (J)

Benzohydrazide (37.4 g) and HBTU (123 g) were dissolved in THF (210 g) at 20-30° C. followed by adding Compound I (98.35 g, 0.25 mol). DIPEA (96.7 g) was charged in the solution and the mixture was stirred for 16 hours at 25-28° C. The mixture was filtered to remove the unrequired solid and then removed the THF about 900 g by vapor. The crude was added acetonitrile (450 g) to form a suspension solution and then stirred about 2-2.5 h, the solution was filtered to collect the product, Compound J (127.9 g, 100%) as a white solid. $^1$H-NMR (CDCl$_3$, 400 MHz): δ 9.17 (brs, 1H), 8.48-8.23 (m, 10H), 7.89 (d, J=7.3 Hz, 2H), 7.77 (d, 8.3 Hz, 2H), 7.53-7.34 (m, 5H), 4.15 (t, J=6.4 Hz, 1H), 2.24-2.19 (m, 1H), 1.24 (s, 9H), 0.93 (d, J=6.9 Hz, 3H), 0.82 (d, J=6.9 Hz, 3H), MS (M+1): 512.

Step 5-5: Preparation of (S)—N-(2-Methyl-1-(4-(5-phenyl-1,3,4-oxadiazol-2-yl)phenyl)propyl)-P,P-diphenylphosphinic amide (K)

Compound J (92 g) was dissolved in dichloromethane (98.8 g) at 0-5° C. followed by adding para-toluenesulfonyl chloride (41.2 g). Triethylamine (54.7 g) was charged in the solution and the mixture was stirred for 6-8 hours at 0-5° C. 1.2 M NaOH aqueous solution (393 mL) was added at the same temperature and stirred for 1 h. The mixture was extracted with additional dichloromethane (100 g) and brine (150 g). The collected organic layer was added anhydrous Na$_2$SO$_4$ (25.00 g) and then the mixture was filtered and the filtrate was dried by vapor. The residue was dissolved in methyl tert-butyl ether (48.7 g) and Heptanes (44.9 g) was added to form a suspension mixture. The mixture was stirred for 4 h and filtered to collect the product, Compound K (66.6 g, 75%) as a white solid. $^1$H-NMR (CDCl$_3$, 400 MHz): δ 8.38-8.13 (m, 10H), 8.15-8.10 (m, 4H), 7.57-7.53 (m, 3H), 7.45 (d, J=8.4 Hz, 2H), 4.22 (t, J=6.3 Hz, 1H), 3.51 (d, J=6.3 Hz, 1H), 2.28-2.21 (m, 1H), 1.26 (s, 9H), 0.98 (d, J=6.9 Hz, 3H), 0.85 (d, J=6.9 Hz, 3-H). MS (M+1): 494.

Step 5-6: Preparation of (S)-2-methyl-1-(4-(5-phenyl-1,3,4-oxadiazol-2-yl)phenyl)propan-1-amine (F) (Compound (3-1))

Compound K (80.4 g) was dissolved in dichloromethane (98.8 g) at 15-25° C. followed by adding con. HCl (162 g). The mixture was stirred for 4 hours at 25-30° C. The reaction solvent was removed by vapor and purified water (162 g) was added. Cooling the temperature down to 0-5° C. and 4M NaOH aqueous solution (454.1) was added to adjust pH=11-12 at 0-15° C. The precipitated solid was filtered and washed additional purified water (130 g). The precipitated solid was recrystallized with MeOH (40.2 g) under 30-40° C. to form a clean solution and stirred, for 4 h at 20-25° C. The solid was filtered again and dried by vacuum to afford Compound F (36 g, 75%).

[Scheme 6]

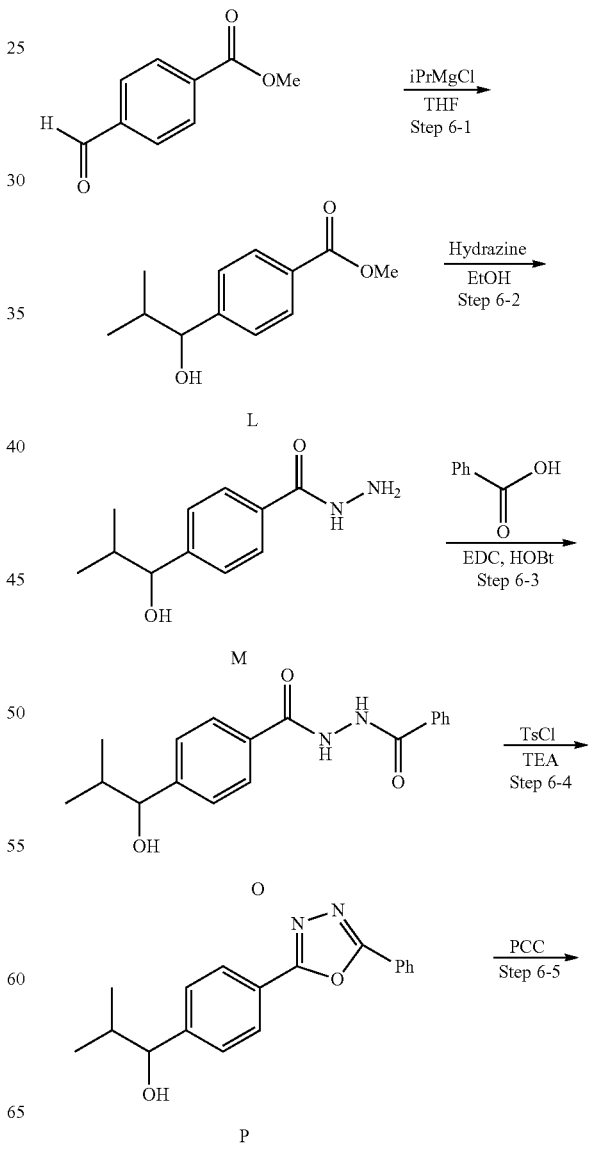

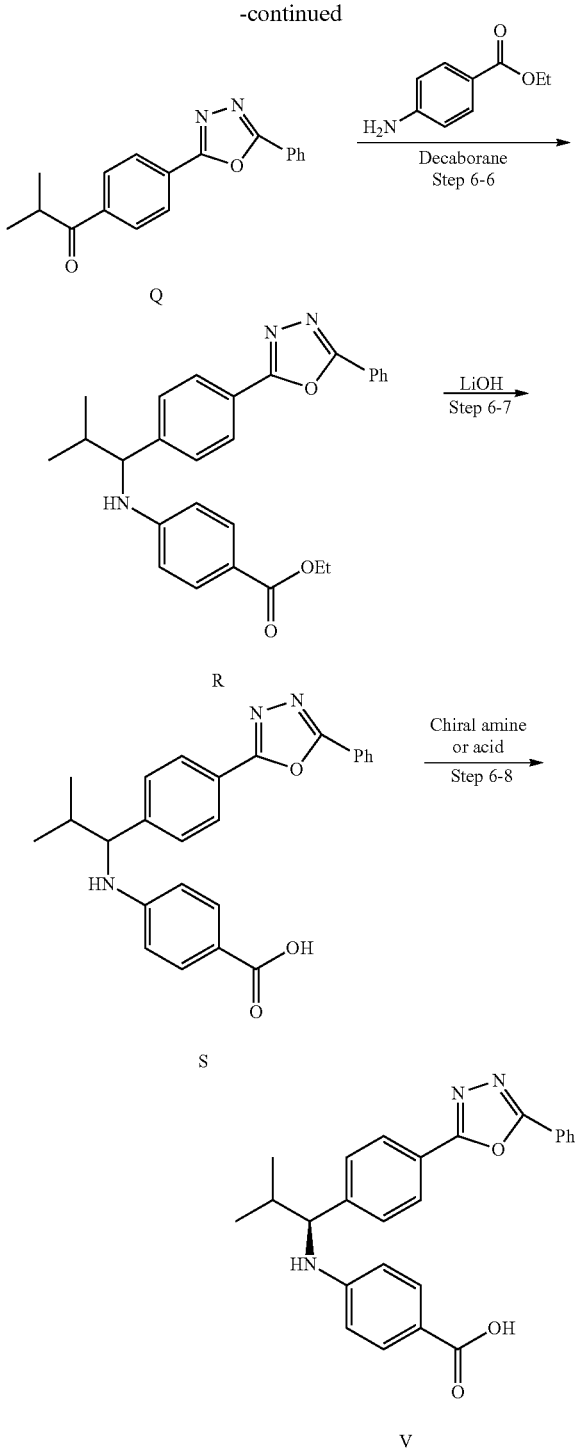

Step 6-1: Preparation of methyl 4-(1-hydroxy-2-methylpropyl)benzoate (L)

A solution of methyl 4-formylbenzoate (9.84 g, 60.0 mmol) in tetrahydrofuran (30 mL) was cooled to −78° C. To this solution was added 2M/isopropylmagnesium chloride (30 mL) dropwise over 20 minutes. The reaction was stirred at −78° C. for 2 h. The reaction was then quenched by addition of saturated aqueous ammonium chloride. This mixture was extracted with ethyl acetate. The organic layer was dried over magnesium sulfate, filtered and concentrated. Purification by silica gel chromatography gave methyl 4-(1-hydroxy-2-methylpropyl)benzoate, Compound L. Colorless oil, yield (4.5 g, 36%).

Step 6-2: Preparation of 4-(1-hydroxy-2-methylpropyl)benzohydrazide (M)

To a solution of methyl 4-(1-hydroxy-2-methylpropyl) benzoate (4.5 g, 21.59 mmol) in absolute EtOH (30 mL) was added hydrazine monohydrate (2.50 g, 50 mmol) at room temperature. The reaction mixture was heated to reflux overnight, then cooled to room temperature and concentrated under reduced pressure. The residue was suspended in 60 mL H$_2$O, filtered, washed with H$_2$O (2×50 mL) and EtOH (2×40 mL) to provide the title Compound M as an off white solid (3.59 g, 80%).

Step 6-3: Preparation of N'-benzoyl-4-(1-hydroxy-2-methylpropyl)benzohydrazide (O)

Compound M (1.04 g, 5 mmole) was added to a solution of benzoic acid (0.67 g, 5.5 mmole), EDCI (1.44 g, 7.5 mmole) and HOBt (1.15 g, 7.5 mmole) in 20 ml DMF. The reaction was stirred at room temperature for overnight then concentrated in vacuum. Water was added to the residue and the aqueous layer was extracted with ethyl acetate. It was further concentrated in vacuo to give white solid product, Compound O (0.99 g, 64%).

Step 6-4: Preparation of 2-methyl-1-(4-(5-phenyl-1,3,4-oxadiazol-2-yl)phenyl)propan-1-ol (P)

Compounds O (0.99 g, 3.2 mmol), TsCl (0.91 g, 4.8 mmol), and TEA (1.5 mL, 9.6 mmol) were mixed in ACN (20 mL) was stirred at room temperature for 1 hr. This reaction solution was concentrated to remove methanol and extracted with EtOAc. The organic layer was washed with water and dried over anhydrous magnesium sulfate. It was filtered, and the solvent was evaporated under reduced pressure. Purification of the crude oil residue by column chromatography (EA:Hex=30:100) afforded white solid product, Compound P (0.76 g, 81%).

Step 6-5: Preparation of 2-methyl-1-(4-(5-phenyl-1,3,4-oxadiazol-2-yl)phenyl)propan-1-one (Q)

Compound P (0.76 g, 2.6 mmol) was dissolved in DCM (26 mL) and pyridinium chlorochromate (1.12 g, 5.2 mmol) was added. The reaction was stirred at room temperature for 2 h. The solution was filtered by Celite-545 and concentrated in vacuum. The residue was purified by flash column chromatography on silica gel (EA:Hexane=10:100). The product, Compound Q was a white solid (0.72 g, 95%).

Step 6-6: Preparation of ethyl 4-((2-methyl-1-(4-(5-phenyl-1,3,4-oxadiazol-2-yl)phenyl) propyl)amino) benzoate (R)

To a solution of Compound Q (17 g, 58 mmol) in methanol (500 mL) was added ethyl 4-aminobenzoate (9 g, 53 mmol) and decaborane (4 g, 32 mmol), and stirred for overnight. The reaction was monitored by TLC. Once the starting material was consumed, then extracted with EtOAc and H$_2$O, dried with Na$_2$SO$_4$ and concentrated under reduced pressure. The resulting residue was purified by column chromatography (EA:Hex=30:100) to afford white solid product, Compound R (18.7 g, 80%).

Step 6-7: Preparation of 4-((2-methyl-1-(4-(5-phenyl-1,3,4-oxadiaziol-2-yl)phenyl)propyl) amino) benzoic acid (S)

Compound R (18.7 g, 42.4 mmol) was dissolved in dioxane (42 mL) followed by addition of LiOH (aq) (2M, 42 mL). The reaction mixture was heat to 60° C. for 1 hr. The reaction was monitored by TLC. With completion of the reaction, the solvent was removed by rotary evaporation and was added $HCl_{(aq)}$ to pH 4~5. The mixture was extracted with EtOAc. The combined organic layer was dried with anhydrous $MgSO_4$ and concentrated in vacuum to give white solid crude, Compound S (17.5 g, 100%).

Step 6-8: Preparation of (S)-4-((2-methyl-1-(4-(5-phenyl-1,3,4-oxadiazol-2-yl)phenyl)propyl) amino) benzoic acid (V)

Compound S (18 g, 43.5 mmol) was dissolved in THE (144 mL) (solvent A) followed by addition of (R)-phenethylamine (6.32 g, 1.2 eq.). The mixture was stirred at 15-25° C. for 12 hr. The precipitated solid was filtered and washed with another THF (18 mL). The cake was dried by vacuum at 45-55° C. for 4 h. The crude product was dissolved in acetone (75 mL) (solvent B) and heated to 45-50° C. for 4 h, then cooled down to 5-10° C. for 6 h. The mixture was filtered and washed with another acetone (21 mL). The pure salt was dried by vacuum at 45-55° C. for 8 h. Finally, the salt (15 g) was dissolved in MeOH (105 mL) followed by addition of pure water (22.5 mL) and citric acid (7.5 g). The mixture was stirred at 15-25° C. for 6 h. The solution was concentrated in vacuum and then pure water (125 mL) was added to slurry the mixture. After 1 h, the mixture was filtered and the solid was washed with pure water (60 mL). The solid was drying under vacuum at 40-45° C. to afford Compound V (6.3 g, 35%, >99.5% e.e.).

In addition, different chiral acids or chiral amines were also examined herein, and the results are shown in the following Table 2.

TABLE 2

| Different reaction conditions used in Step 6-8 | | | | |
|---|---|---|---|---|
| Chiral amine or chiral acid | Solvent A | Solvent B | Yield (%) | e.e. (%) |
| Methanesulfonic acid | THF | — | 95 | 0 |
| (1R)-(−)-10-Camphorsulfonic acid | THF | Acetone | 10 | 80(S-form) |
| (1S)-(−)-10-Camphorsulfonic acid | THF | Acetone | 5 | 85(R-form) |
| L(+)-Tartaric Acid | THF | — | 95 | 0 |
| D(+)-Tartaric Acid | THE | — | 95 | 0 |
| L-(+)-Mandelic acid | THF | — | 95 | 0 |
| L-(−)-Malic acid | THF | — | 95 | 0 |
| (−)-2,3-Dibenzoyl-L-tartaric acid | THF | — | 95 | 0 |
| (R)-phenethylamine | THF | Acetone | 35 | >99.5(S-form) |
| (S)-phenethylamine | THF | Acetone | 20 | 97(R-form) |
| (R)-phenethylamine | THF | EtOAc | 15 | 95(S-form) |
| (R)-phenethylamine | THF | Acetonitrile | 15 | 95(S-form) |
| (R)-phenethylamine | THF | EtOH | 17 | >99.5(S-form) |

[Scheme 6b]

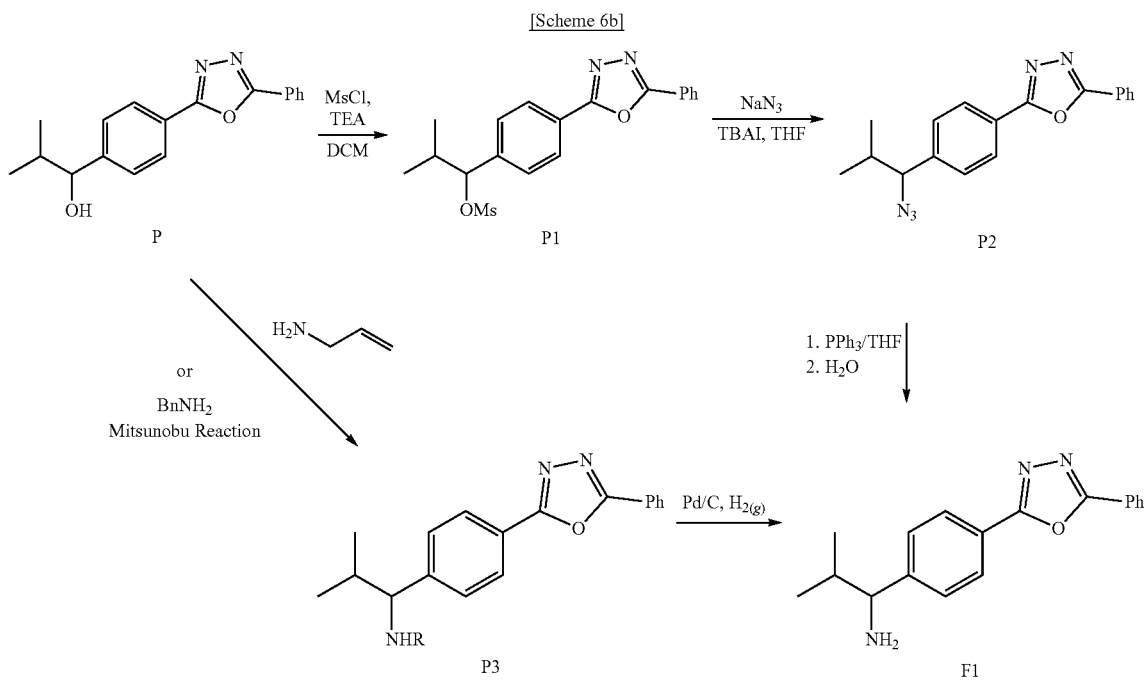

Preparation of (rac)-2-methyl-1-(4-(5-phenyl-1,3,4-oxadiazol-2-yl)phenyl)propan-1-amine (F1)

Compound P could be easy converted to Compound P1 by methanesulfonyl chloride under basic condition. The Compound P1 was treated with sodium azide to produce Compound P2. Otherwise, Compound P also could be converted to Compound P3 by Mitsunobu reaction with allylic amine or benzylic amine. Compound P2 was converted to racematic Compound F1 under Staudinger reaction. Compound P3 was converted to Compound Ft by hydrogenolysis on activated Charcoal. The precipitated solid was filtered and washed additional purified water. The precipitated solid was recrystallized with MeOH under 30-40° C. to form a clean solution and stirred for 4 h at 20-25° C. The solid was filtered again and dried by vacuum to afford Compound F1.

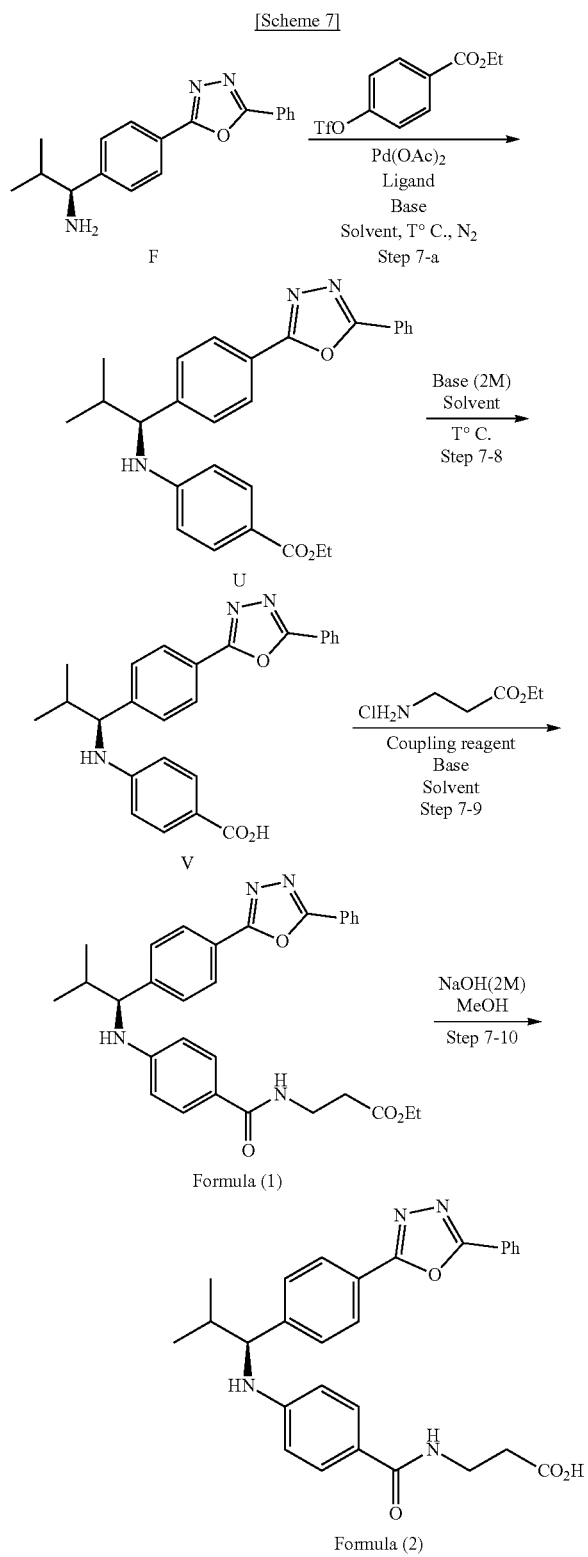

[Scheme 7]

Step 7-a: Preparation of ethyl (S)-4-((2-methyl-1-(4-(5-phenyl-1,4-oxadiazol-2-yl)phenyl) propyl) amino)benzoate (U)

Chiral amine, Compound F (43.3 g, 147 mmol) was dissolved in toluene (350 mL) at 15-25° C. The mixture was replaced with $N_2$ for 3 times. Then the temperature was heated to 40-45° C., 2,2'-bis(diphenylphosphino)-1,1'-binaphthyl (18.6 g) was added followed by adding cesium carbonate (14.4 g). Then the temperature was heated to 60-65° C. and palladium(I) acetate (3.3 g) was added into the mixture and heated to 80-85° C. followed by adding ethyl 4-(((trifluoromethyl)sulfonyl)oxy)benzoate (127.7 g) in toluene (86 mL). The reaction temperature was heated to reflux and stirred for 3 h. After that, the temperature was cooling down to 20-30° C., ethyl acetate (385 g) was added into the mixture and stirred for 0.5 h, then the mixture was filtered by Celite-545. The filtrate was extracted with water (433 mL) and $NaHSO_3$ (130 g), then the organic layer was added the activated carbon (4.3 g) and stirred for 2 h at 80-85° C., the mixture was quickly filtered by Celite-545 again. The solution was extracted with disodium ethylenediaminetetraacetate dihydrate (0.13M, 430 mL). The organic layer was extracted with sat. 220 mL NaCl aqueous solution and then dried with 43 g anhydrous $MgSO_4$. Then the mixture was filtered and dried by vapor. The crude product was recrystallized with 170 g anhydrous ethanol at 75-80° C. for 1 h, then cooling down to 20-25° C., standing at 0-5° C. for 16 h, the solid was collected by filtering and drying under vacuum at 40-45° C. to afford Compound (45 g, 70%) as a white solid, $^1$H-NMR (CDCl$_3$, 400 MHz): δ 8.14-8.08 (m, 4H), 7.78 (d, J=8.8 Hz, 2H), 7.56-7.51 (m, 3H), 7.46 (d, J=8.8 Hz, 2H), 6.47 (d, J=8.8 Hz, 2H), 4.56 (d, J=5.9 Hz, 1H), 4.29-4.24 (m, 3H), 2.16-2.08 (m, 1H), 1.31 (t, J=6.8 Hz, 3H), 1.02 (d, J=6.9 Hz, 3H), 0.97 (d, J=6.9 Hz, 3H). MS (M+1): 442.

In addition, different reaction conditions were also examined herein, and the results are shown in the following Table 3.

TABLE 3

Different reaction conditions used in Step 7-a

| Ligand | Base | Solvent | T (° C.) | Yield (%) | e.e. (%) |
|---|---|---|---|---|---|
| BINAP | Cs$_2$CO$_3$ | Toluene | 110-115 | 70 | >99.5 |
| XPhos | Cs$_2$CO$_3$ | Toluene | 110-115 | 89 | 90 |
| SPhos | Cs$_2$CO$_3$ | Toluene | 110-115 | 77 | 90 |
| CyJohnPhos | Cs$_2$CO$_3$ | Toluene | 110-115 | 80 | <90 |
| BrettPhos | Cs$_2$CO$_3$ | Toluene | 110-115 | 33 | N.A. |
| BINAP | Cs$_2$CO$_3$ | THF | 65-70 | 45 | N.A. |
| BINAP | Cs$_2$CO$_3$ | Dioxane | 100-105 | 50 | N.A. |
| BINAP | NaOtBu | Toluene | 110-115 | 60 | N.A. |
| BINAP | KOtBu | Toluene | 110-115 | 55 | N.A. |

Step 7-8: Preparation of (S)-4-((2-methyl-1-(4-(5-phenyl-1,3,4-oxadiazol-2-yl)phenyl)propyl) amino) benzoic acid (V)

Benzoate, Compound U (80 g, 193 mmol) was dissolved in THF (210 g) at 15-25° C. Methanol (190 g) was added and then the temperature was heat to 40-45° C. LiOH aqueous solution (2 M, 255 g) was charged in the clean solution and stirred for 22 h at 40-45° C. The temperature was cooling down to 20-25° C. Pure water (360 mL) was added in the solution and then extracted with ethyl acetate (30 g) and heptanes (120 g), the organic layer was removed, citric acid (27 g) was added to the water layer and changed pH to 4-5. The organic solvent of the solution was removed by vapor under 40-45° C., then cooling it down to 10-15° C. for 4 h. The mixture was filtered and washed by water (320 mL). Solid was collected and dried by vacuum under 40-45° C. to afford Compound V (74 g, 98%) as a white solid. $^1$H-NMR (CDCl$_3$, 400 MHz): δ 8.11-8.04 (m, 4H), 7.64-7.56 (m, 7H), 6.94 (d, J=7.8 Hz, 1H), 6.60 (d, J=8.8 Hz, 2H), 4.28 (t, 7.8 Hz, 1H), 2.09-2.01 (m, 1H), 1.03 (d, J=6.9 Hz, 3H), 0.81 (d, J=6.9 Hz, 3H), MS (M+1): 414.

In addition, different reaction conditions were also examined herein, and the results are shown in the following Table 4.

TABLE 4

Different reaction conditions used in Step 7-8

| Base | Solvent | T (° C.) | Time (h) | Yield (%) |
|---|---|---|---|---|
| NaOH | EtOH | 40-45 | 16 | 80 |
| NaOH | EtOH | 60-65 | 4 | 70 |
| NaOH | EtOH | 75-80 | 2 | 60 |
| NaOH | MeOH/THF | 40-45 | 16 | 85 |
| NaOH | MeOH/THF | 50-55 | 12 | 75 |
| LiOH | EtOH | 40-45 | 8 | 80 |
| LiOH | EtOH | 60-65 | 3 | 65 |
| LiOH | MeOH/THF | 40-45 | 16 | 98 |
| LiOH | MeOH/THF | 50-55 | 12 | 85 |

Step 7-9: Preparation of ethyl (S)-3-(4-((2-methyl-1-(4-(5-phenyl-1,3,4-oxadiazol-2-yl)phenyl) propyl) amino)benzamido)propanoate (Formula (1))

Benzoic acid, Compound V (120 g, 234 mmol) was dissolved in DMF (793 g) at 15-20° C. under N$_2$ protection. The temperature was cooling down to 0-10° C. following by adding BHTU (142.8 g). The mixture was stirred for 10 minute at 0-10° C., and then ethyl 3-aminopropanoate hydrochloride (60 g) was added. Finally, DIPEA (112.8 g) was dropped into the reaction within 0.5 h. The mixture was stirred for another 4 hours at 0-10° C., then dropped into a solution of pure water (3700 mL) and sodium bicarbonate (166 g) about 0.5 h to form a suspension solution. Then the solution was filtered and washed the cake by another pure water (150 mL). The cake was dissolved in ethyl acetate (756 g) at 0-10° C., then HCl (1N, 120 mL) was added and stirred for 0.5 h. Removing the water layer, the organic layer was extracted with 4.8 g sodium bicarbonate aqueous solution (in 120 mL water). The organic layer was extracted with sat, NaCl aqueous solution (360 mL) and then dried with anhydrous MgSO$_4$. (65 g), Then the mixture was filtered and dried by vapor. The crude product was recrystallized with anhydrous ethanol (240 g) at 75-80° C. for 1 h, then cooling down to 20-25° C. and standing for 16 h, the solid was collected by filtering and drying under vacuum at 40-45° C. to afford Compound of Formula (1) (105 g, 70%) as a white solid. $^1$H-NMR (CDCl$_3$, 400 MHz): δ 8.13-8.07 (m, 4H), 7.56-7.51 (m, 5H), 7.45 (d, J=8.8 Hz, 2H), 6.60 (t, J=5.8 Hz, 1H), 6.48 (d, J=8.8 Hz, 2H), 4.26 (d, J=5.8 Hz, 1H), 4.12 (q, J=6.8 Hz, 2H), 3.66-3.62 (m, 2H), 2.57 (t, J=5.8 Hz, 2H), 2.14-2.10 (m, 1H), 1.23 (t, J=6.8 Hz, 3H), 1.03 (d, J=6.9 Hz, 3H), 0.97 (d, J=6.9 Hz, 3H). MS (M+1): 513.

In addition, different reaction conditions were also examined herein, and the results are shown in the following Table 5.

TABLE 5

Different reaction conditions used in Step 7-9

| Coupling Reagent | Solvent | Time (h) | Yield (%) |
|---|---|---|---|
| EDCI/HOBt | THF | 12 | 70 |
| EDCI/HOBt | DMF | 8 | 75 |
| HBTU | DMF | 4 | 70 |
| HBTU | THF | 8 | 72 |
| HATU | DMF | 4 | 65 |
| CDMT | DMF | 4 | 50 |
| PyBOP | THF | 8 | 82 |

Step 7-10: Preparation of (S)-3-(4-((2-methyl-1-(4-(5-phenyl-1,3,4-oxadiazol-2-yl)phenyl) propyl)amino)benzamido)propanoic acid (Formula (2))

Compound of Formula (1) (62.9 g) was dissolved in MeOH (250 mL) or MeOH/THF (125/125 mL) at 15-25° C. NaOH(aq) (2 M, 123 mL) was added into the mixture and stirred for 15 h. The reaction solvent was removed by rotary evaporation, and ethyl acetate (500 mL) was added into the residue and extracted with a citric acid aqueous solution (38.6 L). The organic layer was extracted with sat. NaCl aqueous solution (180 mL) and then dried with anhydrous MgSO$_4$ (30 g). Then the mixture was filtered and dried by vapor. The crude product was recrystallized with anhydrous ethanol (120 g) at 75-80° C. for 1 h, then cooling down to 20-25° C. and standing for 16 h, the solid was collected by filtering and drying under vacuum at 40-45° C. to afford Compound of Formula (2) (45 g, 75%) as a white solid. $^1$H-NMR (DMSO-d$_6$, 400 MHz): δ 8.13-7.96 (m, 5H), 7.65-7.59 (m, 4H), 7.49 (d, J=8.8 Hz, 2H), 6.66 (d, J=7.8 Hz, 1H), 6.57 (d, J=8.8 Hz, 2H), 4.29 (d, J=5.8 Hz, 1H), 3.38-3.33 (m, 2H), 2.40 (t, J=5.8 Hz, 2H), 2.08-2.03 (m, 1H), 1.04 (d, J=6.9 Hz, 3H), 0.83 (d, J=6.9 Hz, 3H), MS (M+1): 485.

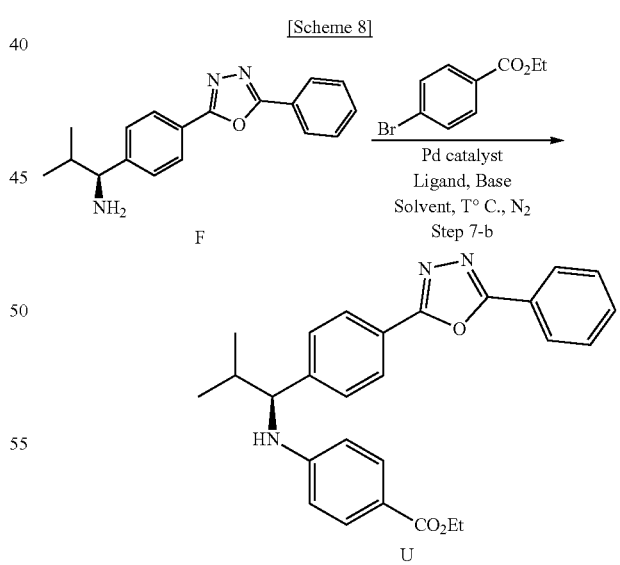

Step 7-b: Preparation of Ethyl (S)-4-((2-methyl-1-(4-(5-phenyl-1,3,4-oxadiazol-2-yl)phenyl) propyl) amino)benzoate (U)

Chiral amine, Compound F (50 g, 170 mmol) was dissolved in toluene (600 mL) at 15-25° C. The mixture was replaced with N₂ for 3 times. Then the temperature was heated to 40-45° C., 2,2'-bis(diphenylphosphino)-1,1'-binaphthyl (21.2 g) was added followed by adding cesium carbonate (166 g). Then the temperature was heated to 60-65° C. and palladium(II) acetate (1.9 g) was added into the mixture and heated to 80-85° C. followed by adding ethyl 4-bromobenzoate (46.8 g). The reaction temperature was heated to reflux and stirred for 4 h. After that, the temperature was cooling down to 20-30° C., ethyl acetate (440 g) was added into the mixture and stirred for 5 minutes, then the mixture was filtered by Celite-545. The filtrate was extracted with water (500 mL) and NaHSO₃ (150 g), then the organic layer was added the activated carbon (0.43 g) and stirred for 10 minutes at 80-85° C., and the mixture was quickly filtered by Celite-545 again. The solution was extracted with Na₂EDTA (0.13M, 500 mL)/H₂O/disodium ethylenediaminetetraacetate dihydrate (1:2:1). The organic layer was extracted with sat. NaCl aqueous solution (250 mL) and then dried with anhydrous MgSO₄ (50 g). Then the mixture was filtered and dried by vapor. The crude product was recrystallized with anhydrous ethanol (50 g) at 75-80° C. for 1 h, then cooling down to 20-25° C., standing at 0-5° C. for 16 h, the solid was collected by filtering and drying under vacuum at 40-45° C. to afford Compound U (56 g, 75%).

In addition, different reaction conditions were also examined herein, and the results are shown in the following Table 6.

TABLE 6

Different reaction conditions in Step 7-b

| Pd cat. | Ligand | Base | Solvent | T (° C.) | Yield (%) | e.e. (%) |
|---|---|---|---|---|---|---|
| Pd(OAc)₂ | BINAP | Cs₂CO₃ | Toluene | 110-115 | 75 | >99.5 |
| Pd(OAc)₂ | XPhos | Cs₂CO₃ | Toluene | 110-115 | 84 | 90 |
| Pd(OAc)₂ | SPhos | Cs₂CO₃ | Toluene | 110-115 | 70 | 90 |
| Pd(OAc)₂ | CyJohnPhos | Cs₂CO₃ | Toluene | 110-115 | 78 | <90 |
| Pd(OAc)₂ | BrettPhos | Cs₂CO₃ | Toluene | 110-115 | 30 | N.A. |
| Pd₂(dba)₃ | XPhos | Cs₂CO₃ | Toluene | 110-115 | 95 | 92 |
| Pd(OAc)₂ | BINAP | Cs₂CO₃ | THF | 65-70 | N.A. | N.A. |
| Pd(OAc)₂ | BINAP | Cs₂CO₃ | Dioxane | 100-105 | 45 | N.A. |
| Pd(OAc)₂ | BINAP | NaOtBu | Toluene | 110-115 | 65 | N.A. |
| Pd(OAc)₂ | BINAP | KOtBu | Toluene | 110-115 | 50 | N.A. |

[Scheme 9]

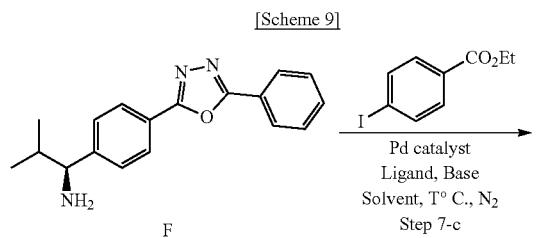

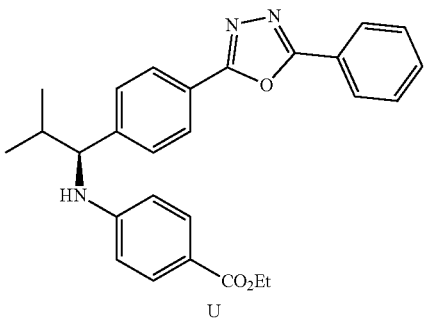

Step 7-c: Preparation of ethyl (S)-4-((2-methyl-1-(4-(5-phenyl-1,4-oxadiazol-2-yl)phenyl) propyl) amino)benzoate (U)

Chiral amine, Compound F (50 g, 170 mmol) was dissolved in toluene (600 mL) at 15-25° C. The mixture was replaced with N₂ for 3 times. Then the temperature was heated to 40-45° C., 2,2'-bis(diphenylphosphino)-1,1'-binaphthyl (21.2 g) was added followed by adding cesium carbonate (166 g). Then the temperature was heated to 60-65° C. and palladium(II) acetate (1.9 g) was added into the mixture and heated to 80-85° C. followed by adding ethyl 4-iodobenzoate (56.3 g). The reaction temperature was heated to reflux and stirred for 4 h. After that, the temperature was cooling down to 20-30° C., ethyl acetate (440 g) was added into the mixture and stirred for 5 minutes, then the mixture was filtered by Celite-545. The filtrate was extracted with water (500 mL) and NaHSO₃ (150 g), then the organic layer was added with the activated carbon (0.43 g) and stirred for 10 minutes at 80-85° C., the mixture was quickly filtered by Celite-545 again. The solution was extracted with disodium ethylenediaminetetraacetate dihydrate (0.13M, 500 mL). The organic layer was extracted with sat. NaCl aqueous solution (250 mL) and then dried with anhydrous MgSO₄ (50 g). Then the mixture was filtered and dried by vapor. The crude product was recrystallized with anhydrous ethanol (50 g) at 75-80° C. for 1 h, then cooling down to 20-25° C., standing at 0-5° C. for 16 h, and the solid was collected by filtering and drying under vacuum at 40-45° C. to afford Compound U (36.5 g, 49%).

In addition, different reaction conditions were also examined herein, and the results are shown in the following Table 7.

TABLE 7

Different reaction conditions in Step 7-c

| Pd cat. | Ligand | Base | Solvent | T (° C.) | Yield (%) | e.e. (%) |
|---|---|---|---|---|---|---|
| Pd(OAc)₂ | BINAP | Cs₂CO₃ | Toluene | 110-115 | 49 | 97 |
| Pd(OAc)₂ | XPhos | Cs₂CO₃ | Toluene | 110-115 | 68 | 94 |
| Pd₂(dba)₃ | XPhos | Cs₂CO₃ | Toluene | 110-115 | 55 | 90 |
| Pd(OAc)₂ | BINAP | Cs₂CO₃ | THF | 65-70 | N.A. | N.A. |
| Pd(OAc)₂ | BINAP | Cs₂CO₃ | Dioxane | 100-105 | 20 | N.A. |
| Pd(OAc)₂ | BINAP | NaOtBu | Toluene | 110-115 | 40 | N.A. |
| Pd(OAc)₂ | BINAP | KOtBu | Toluene | 110-115 | 35 | N.A. |

[Scheme 10]

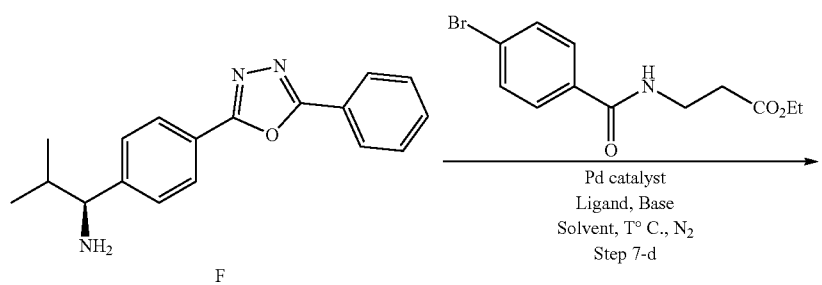

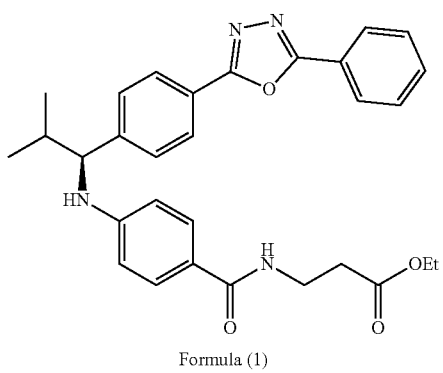

Formula (1)

Step 7-d: Preparation of ethyl (S)-3-(4-((2-methyl-1-(4-(5-phenyl-1,3,4-oxadiazol-2-yl) phenyl)propyl)amino)benzamido)propanoate (Formula (1))

Chiral amine, Compound F (5 g, 17 mmol) was dissolved in toluene (60 L) at 15-25° C. The mixture was replaced with $N_2$ for 3 times. Then the temperature was heated to 40-45° C., and 2,2'-bis(diphenylphosphino)-1,1'-binaphthyl (2.12 g) was added, followed by adding cesium carbonate (16.6 g). Then the temperature was heated to 60-65° C. and palladium (II) acetate (0.38 g) was added into the mixture and heated to 80-85° C. followed by adding ethyl 3-(4-bromobenzamido) propanoate (6.1 g). The reaction temperature was heated to reflux and stirred for 2.5 h. The mixture was added with palladium(II) acetate (0.2 g) and stirred for another 2 h. After that, the temperature was cooling down to 20-30° C., ethyl acetate (44 g) was added into the mixture and stirred for 5 minutes, then the mixture was filtered by Celite-545. The filtrate was extracted with water (50 mL) and $NaHSO_3$ (15 g), then the organic layer was extracted with disodium ethylenediaminetetraacetate dihydrate (0.13M, 50 mL), The organic layer was extracted with sat. NaCl aqueous solution (25 mL) and then dried with anhydrous $MgSO_4$ (5 g). Then the mixture was filtered and dried by vapor. The crude product was recrystallized with anhydrous ethanol (10 mL) at 75-80° C. for 1 h, then cooling down to 20-25° C., standing at 0-5° C. for 16 h, and the solid was collected by filtering and drying under vacuum at 40-45° C. to afford Compound of Formula (1) (5.6 g, 64%).

In addition, different reaction conditions were also examined herein, and the results are shown in the following Table 8.

TABLE 8

Different reaction conditions in Step 7-d

| Ligand | Base | Solvent | T (° C.) | Yield (%) | e.e. (%) |
|---|---|---|---|---|---|
| BINAP | $Cs_2CO_3$ | Toluene | 110-115 | 64 | >99.5 |
| XPhos | $Cs_2CO_3$ | Toluene | 110-115 | 60 | 94 |
| BINAP | $Cs_2CO_3$ | THF | 65-70 | N.A. | N.A. |
| BINAP | $Cs_2CO_3$ | Dioxane | 100-105 | 30 | N.A. |
| BINAP | NaOtBu | Toluene | 110-115 | 47 | N.A. |
| BINAP | KOtBu | Toluene | 110-115 | 45 | N.A. |

[Scheme 11]

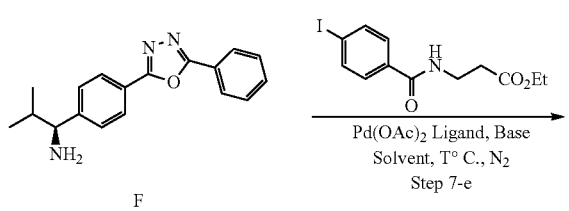

-continued

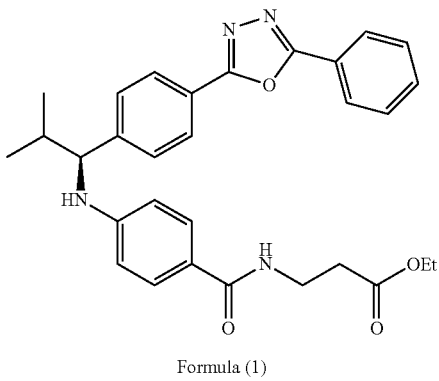

Formula (1)

Step 7-e: Preparation of ethyl (S)-3-(4-((2-methyl-1-(4-(5-phenyl-1,3,4-oxadiazol-2-yl)phenyl) propyl) amino)benzamido)propanoate (Formula (1))

Chiral amine, Compound F (5 g, 17 mmol) was dissolved in toluene (60 mL) at 15-25° C. The mixture was replaced with $N_2$ for 3 times. Then the temperature was heated to 40-45° C., 2,2'-bis(diphenylphosphino)-1,1'-binaphthyl (2.12 g) was added followed by adding cesium carbonate (16.6 g). Then the temperature was heated to 60-65° C. and palladium(II) acetate (0.38 g) was added into the mixture and heated to 80-85° C. followed by adding ethyl 3-(4-iodobenzamido) propanoate (7.1 g). The reaction temperature was heated to reflux and stirred for 2.5 h. The mixture was added with palladium(II) acetate (0.2 g) and stirred for another 2 h. After that, the temperature was cooling down to 20-30° C., ethyl acetate (44 g) was added into the mixture and stirred for 5 minutes, then the mixture was filtered by Celite-545. The filtrate was extracted with water (50 mL) and $NaHSO_3$ (15 g), and then the organic layer was extracted with disodium ethylenediaminetetraacetate dihydrate (0.13M, 50 mL). The organic layer was extracted with sat. NaCl aqueous solution (25 mL) and then dried with anhydrous $MgSO_4$ (5 g). Then the mixture was filtered and dried by vapor. The crude product was purified by flash-chromatography (EA:Hex=55%~60%) to afford. Compound of Formula (1) (1.3 g, 15%).

In addition, different reaction conditions were also examined herein, and the results are shown in the following Table 9.

TABLE 9

Different reaction conditions in Step 7-e

| Ligand | Base | Solvent | T (° C.) | Yield (%) | e.e. (%) |
|---|---|---|---|---|---|
| BINAP | $Cs_2CO_3$ | Toluene | 110-115 | 15 | >99.5 |
| XPhos | $Cs_2CO_3$ | Toluene | 110-115 | 50 | 94 |
| BINAP | $Cs_2CO_3$ | THF | 65-70 | N.A. | N.A. |
| BINAP | $Cs_2CO_3$ | Dioxane | 100-105 | N.A. | N.A. |
| BINAP | NaOtBu | Toluene | 110-115 | N.A. | N.A. |
| BINAP | KOtBu | Toluene | 110-115 | N.A. | N.A. |

Example 2—Preparation of Crystalline Form of Compound of Formula (1)

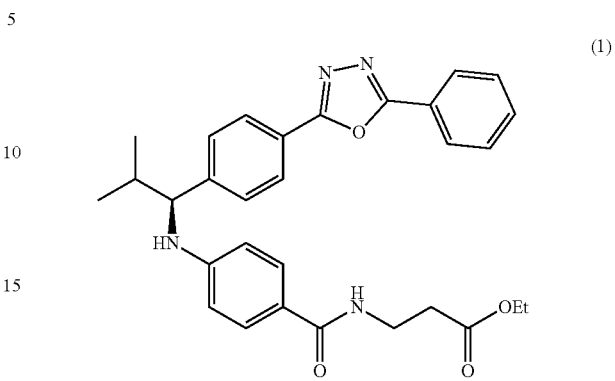

(1)

Ethyl (S)-3-(4-((2-methyl-1-(4-(5-phenyl-1,3,4-oxadiazol-2-yl)phenyl)propyl)amino) benzamido)propanoate (10 g) was dissolved in EtOH (25 mL) and then heated to reflux and kept the temperature for 1 h, then cooling down to 5-10° C. and kept at the temperature for 12 h, and the solid was formed. Then the solid was filtered and dried by vacuum at 45-50° C. to afford the crystalline form. Yield: 5 g.

The XRD pattern of the obtained crystalline form of the compound of Formula (1) was acquired by using Balker D2 Phaser, and the result is shown in FIG. 1. The XRD pattern comprises peaks at about 14.2, 15.6, 16.4, 17.4, 20.1, 20.5, 21.2 and 21.7° 2θ. In addition, the DSC data of the obtained crystalline form of the compound of Formula (1) was acquired by using Perkin Elmer Pyris 1, and the obtained DSC curve indicates that the melting endotherm peak of the obtained crystalline form of the compound of Formula (1) is at about 137.7° C.

Example 3—Preparation of Crystalline Form of Compound of Formula (1)

Ethyl (S)-3-(4-((2-methyl-1-(4-(5-phenyl-1,3,4-oxadiazol-2-yl)phenyl)propyl)amino) benzamido)propanoate (30 g) was dissolved in ethyl acetate (60 mL) at 20-30° C. and kept at the temperature for 3-4 h, and the solid was formed. Then the solid was filtered and dried by vacuum at 45-50° C. to afford the crystalline form. Yield: 15 g.

The XRD pattern and DSC curve of the crystalline form of the compound of Formula (1) in the present example were obtained by the similar methods used in Example 2.

Figure 2:
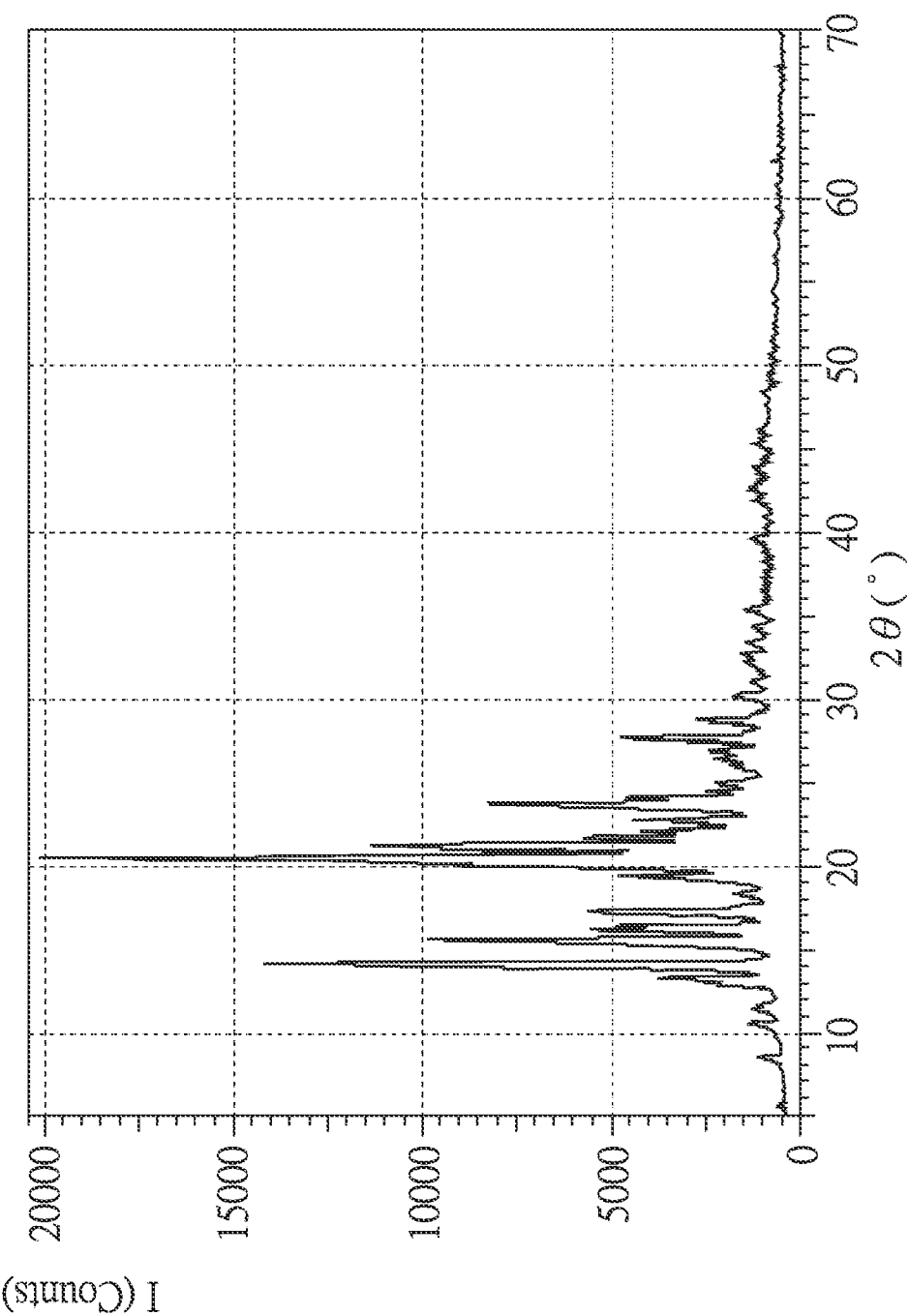
FIG. 2 shows an XRD pattern of a crystalline form of a compound of formula (1) according to Example 3 of the present disclosure.

The XRD pattern of the obtained crystalline form of the compound of Formula (1) is shown in FIG. 2, which comprises peaks at about 14.2, 15.6, 16.4, 17.4, 20.1, 20.5, 21.2 and 23.7° 2θ. In addition, the Obtained DSC curve indicates that the melting endotherm peak of the obtained crystalline form of the compound of Formula (1) is at about 136.1° C.

Example 4—Preparation of Crystalline Form of Compound of Formula (1)

Ethyl (S)-3-(4-((2-methyl-1-(4-(5-phenyl-1,3,4-oxadiazol-2-yl)phenyl)propyl)amino) benzamido)propanoate (10 g) was dissolved in Acetone (30 mL) and then heated to reflux and kept the temperature for 1 h, then cooling down to 15-25° C. and kept at the temperature for 12 h, and the solid was formed. Then the solid was filtered and dried by vacuum at 45-50° C. to afford the crystalline form. Yield: 3 g.

The XRD pattern and DSC curve of the crystalline form of the compound of Formula (1) in the present example were obtained by the similar methods used in Example 2.

Figure 3:
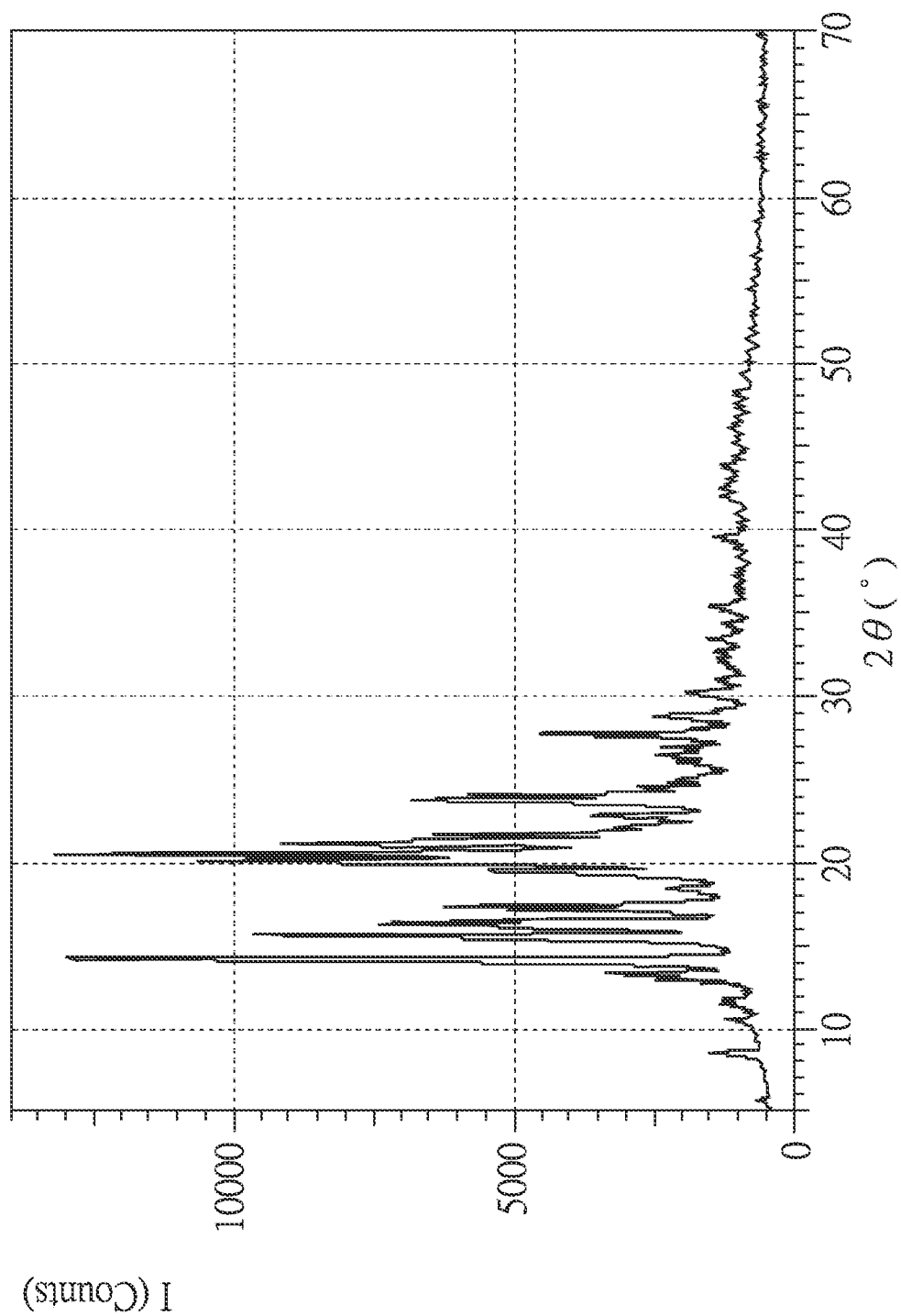
FIG. 3 shows an XRD pattern of a crystalline form of a compound of formula (1) according to Example 4 of the present disclosure.

The XRD pattern of the obtained crystalline form of the compound of Formula (1) is shown in FIG. 3, which comprises peaks at about 14.2, 15.6, 16.4, 20.1, 20.5, 21.2, 21.7 and 23.7° 2θ. In addition, the obtained DSC curve indicates that the melting endotherm peak of the obtained crystalline form of the compound of Formula (1) is at about 137.9° C.

Example 5—Preparation of Crystalline Form of Compound of Formula (1)

Ethyl (S)-3-(4-((2-methyl-1-(4-(5-phenyl-1,3,4-oxadiazol-2-yl)phenyl)propyl)amino) benzamido)propanoate (10 g) was dissolved in ethyl acetate (30 mL) and then heated to reflux and kept the temperature for 1 h, and n-Heptane (45 mL) was added at that temperature within 5 minutes. The mixture was stirred for another 1 h, then cooling down to 15-25° C. and kept at the temperature for 12 h, and the solid was formed. Then the solid was filtered and dried by vacuum at 45-50° C. to afford the crystalline form. Yield: 9.5 g.

The XRD pattern and DSC curve of the crystalline form of the compound of Formula (1) in the present example were obtained by the similar methods used in Example 2.

Figure 4:
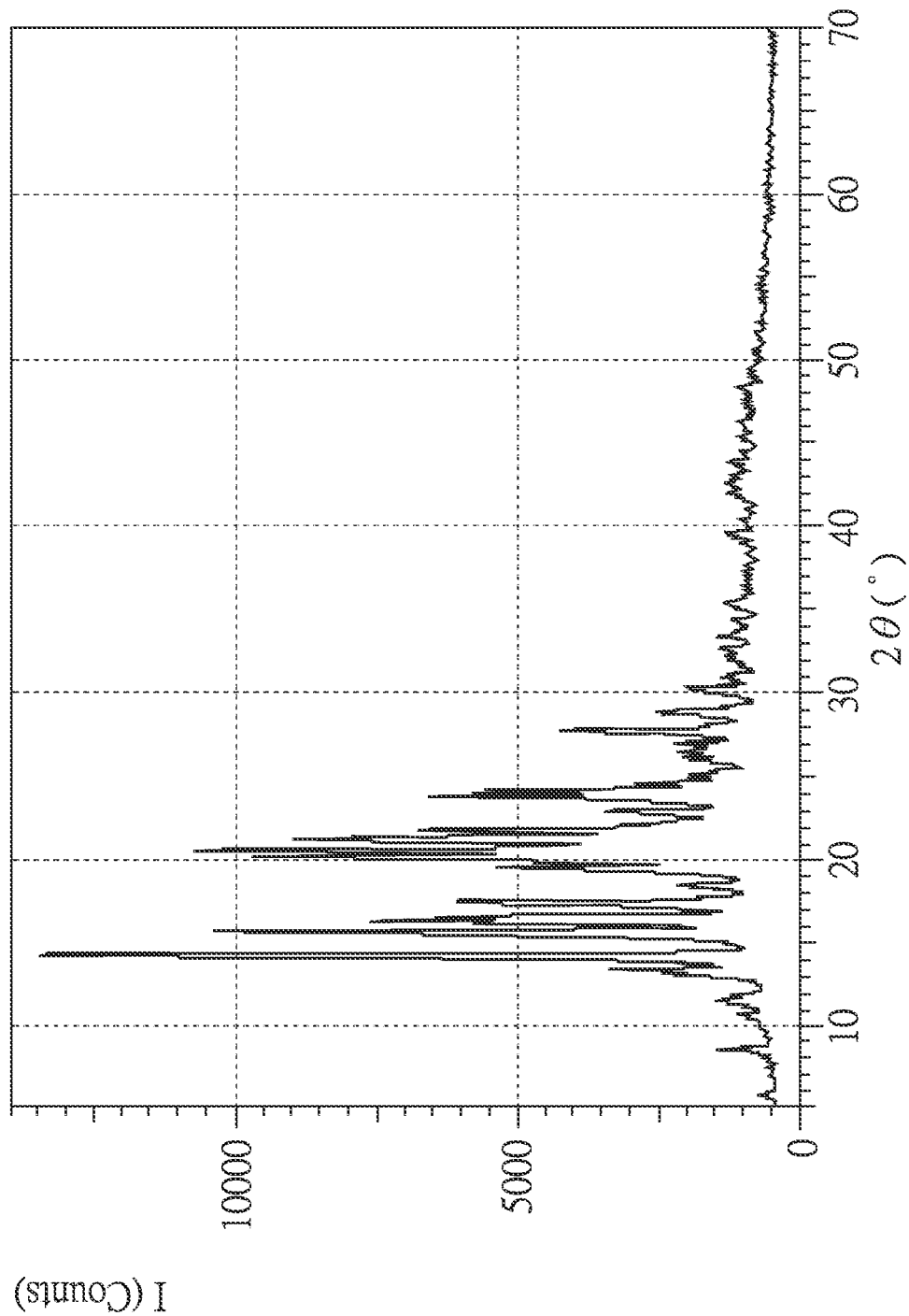
FIG. 4 shows an XRD pattern of a crystalline form of a compound of formula (2) according to Example 5 of the present disclosure.

The XRD pattern of the obtained crystalline form of the compound of Formula (1) is shown in FIG. 4, which comprises peaks at about 14.2, 15.6, 16.4, 17.3, 20.1, 20.5, 21.2 and 23.7° 2θ. In addition, the obtained DSC curve indicates that the melting endotherm peak of the obtained crystalline form of the compound of Formula (1) is at about 136.2° C.

Examples 6-11 and Comparative Examples 1-5—Preparation of Crystalline Form of Compound of Formula (1)

In Examples 6-11 and Comparative Examples 1-5 (Comp Examples 1-5 in Table 10), different recrystallization conditions were used to prepare the crystalline form of the compound of Formula (1). The solvents used in Examples 6-11 and Comparative Examples 1-5 are listed in Table 10 below, and the methods used in Examples 6-11 and Comparative Examples 1-5 are similar to the methods used in Examples 2-5 and are not described again. In Table 10, "O" and "X" in the column of DSC respectively means that the melting endotherm peak was observed or not. Similarly, "O" or "X" in the column of XRD peaks respectively means that the XRD peaks were observed or not.

TABLE 10

Different recrystallization conditions of the crystalline form of the compound of Formula (1)

| | Solvent A | Solvent B | DSC | Yield (%) | XRD peaks |
|---|---|---|---|---|---|
| Example 6 | Acetonitrile | — | O | 35 | O |
| Example 7 | 1-Butanol | — | O | 90 | O |
| Example 8 | Butyl Acetate | — | O | 85 | O |
| Example 9 | Isopropanol | — | O | 80 | O |
| Example 10 | tert-Butanol | — | O | 84 | O |
| Example 11 | Ethanol | n-Heptane | O | 70 | O |
| Comp Exmaple 1 | THF | — | X | — | X |
| Comp Exmaple 2 | 1,4-Dioxane | — | X | — | X |
| Comp Exmaple 3 | Dichloromethane | — | X | — | X |
| Comp Exmaple 4 | Methanol | — | X | — | X |
| Comp Exmaple 5 | Toluene | — | X | — | X |

Example 12—Preparation of Crystalline Form of Compound of Formula (2)

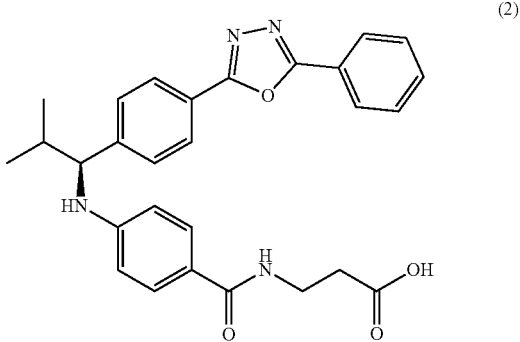 [SMILES: CCOC(=O)CCNC(=O)c1ccc(N[C@H](c2ccc(-c3nnc(-c4ccccc4)o3)cc2)C(C)C)cc1]

(2)

(S)-3-(4(2-methyl-1-(4-(5-phenyl-1,3,4-oxadiazol-2-yl)phenyl)propyl)amino) benzamido)propanoic acid (5 g) was dissolved in EtOH (30 mL) and then heated to reflux and kept the temperature for 1 h, then cooling down to 15-25° C. and kept at the temperature for 12 h, and the solid was formed. Then the solid was filtered and dried by vacuum at 45-50° C. to afford the crystalline form. Yield: 1.7 g.

The XRD pattern and DSC curve of the crystalline form of the compound of Formula (2) in the present example were obtained by the similar methods used in Example 2.

The XRD pattern of the obtained crystalline form of the compound of Formula (2) is shown in FIG. 5, which comprises peaks at about 14.5, 18.6, 19.9, 20.1, 21.8, 22.0, 23.8 and 25.0° 2θ. In addition, the obtained DSC curve indicates that the melting endotherm peak of the obtained crystalline form of the compound of Formula (2) is at about 91.7° C. (minor peak) and 168.4° C. (major peak).

Example 13—Preparation of Crystalline Form of Compound of Formula (2)

(S)-3-(4-((2-methyl-1-(4-(5-phenyl-1,3,4-oxadiazol-2-yl)phenyl)propyl)amino) benzamido)propanoic acid (5 g) was dissolved in acetone (40 mL) and then heated to reflux and kept the temperature for 1 h, then cooling down to 15-25° C. and kept at the temperature for 12 h, and the solid was formed. Then the solid was filtered and dried by vacuum at 45-50° C. to afford the crystalline form. Yield: 3 g.

The XRD pattern and DSC curve of the crystalline form of the compound of Formula in the present example were obtained by the similar methods used in Example 2.

The XRD pattern of the obtained crystalline form of the compound of Formula (2) is shown in FIG. 6, which comprises peaks at about 14.5, 18.6, 20.2, 21.7, 23.8, 25.0, 28.5 and 31.0° 2θ. In addition, the obtained DSC curve indicates that the melting endotherm peak of the obtained crystalline form of the compound of Formula (2) is at about 86.7° C. (minor peak) and 169.2° C. (major peak).

Example 14—Preparation of Sodium Salt of Compound of Formula (2)

(S)-3-(4-((2-methyl-1-(4-(5-phenyl-1,3,4-oxadiazol-2-yl)phenyl)propyl)amino) benzamido)propanoic acid (10 g) was dissolved in anhydrous EtOH (80 mL) at 15-25° C. and then NaOH (0.85 g) was added. The mixture was stirred for 12 h, and then the solution was dried by vacuum at 40-45° C. Ethyl acetate (80 mL) was added into the residue and stirred for 2 h, and the mixture was filtered and afforded the sodium salt. Yield: 8 g.

The XRD pattern and DSC curve of the sodium salt of the compound of Formula (2) in the present example were obtained by the similar methods used in Example 2.

Figure 7:
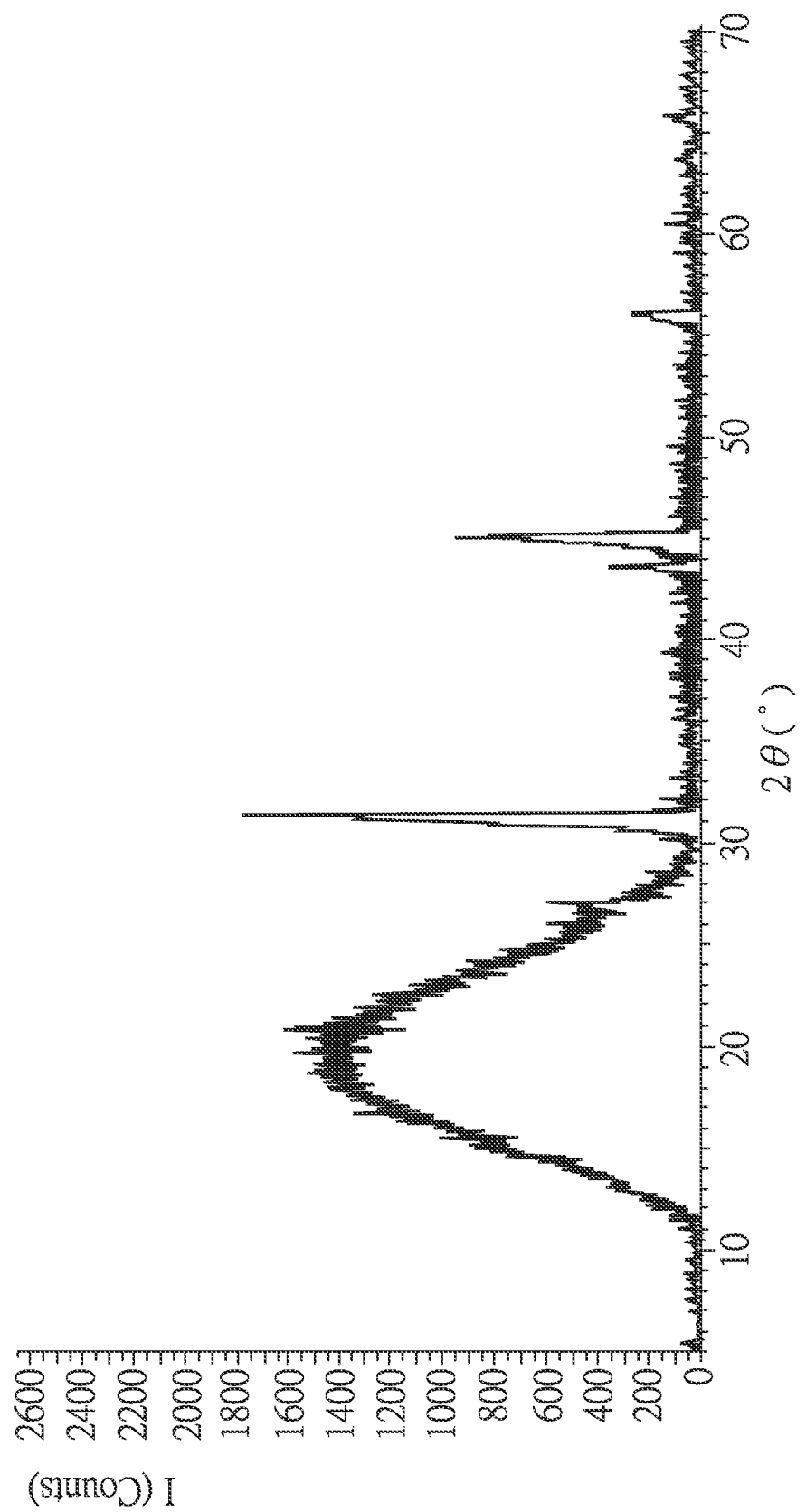
FIG. 7 shows an XRD pattern of a sodium salt of a compound of formula (2) according to Example 14 of the present disclosure.

The XRD pattern of the obtained sodium salt of the compound of Formula (2) is shown in FIG. 7. No significant peaks were found in the DSC curve. In addition, the TGA result indicates a weight loss of about 4% from ambient temperature to about 175° C.

Example 15—Preparation of Potassium Salt of Compound of Formula (2)

(S)-3-(4-((2-methyl-1-(4-(5-phenyl-1,3,4-oxadiazol-2-yl)phenyl)propyl)amino) benzamido)propanoic acid (10 g) was dissolved in anhydrous EtOH (50 mL) at 15-25° C. and then KOH (1.15 g) was added. The mixture was stirred for 12 h, and then the solution was dried by vacuum at 40-45° C. Ethyl acetate (80 mL) was added into the residue and stirred for 2 h, and the mixture was filtered and afforded the potassium salt. Yield: 10 g.

The XRD pattern and DSC curve of the potassium salt of the compound of Formula (2) in the present example were obtained by the similar methods used in Example 2.

Figure 8:
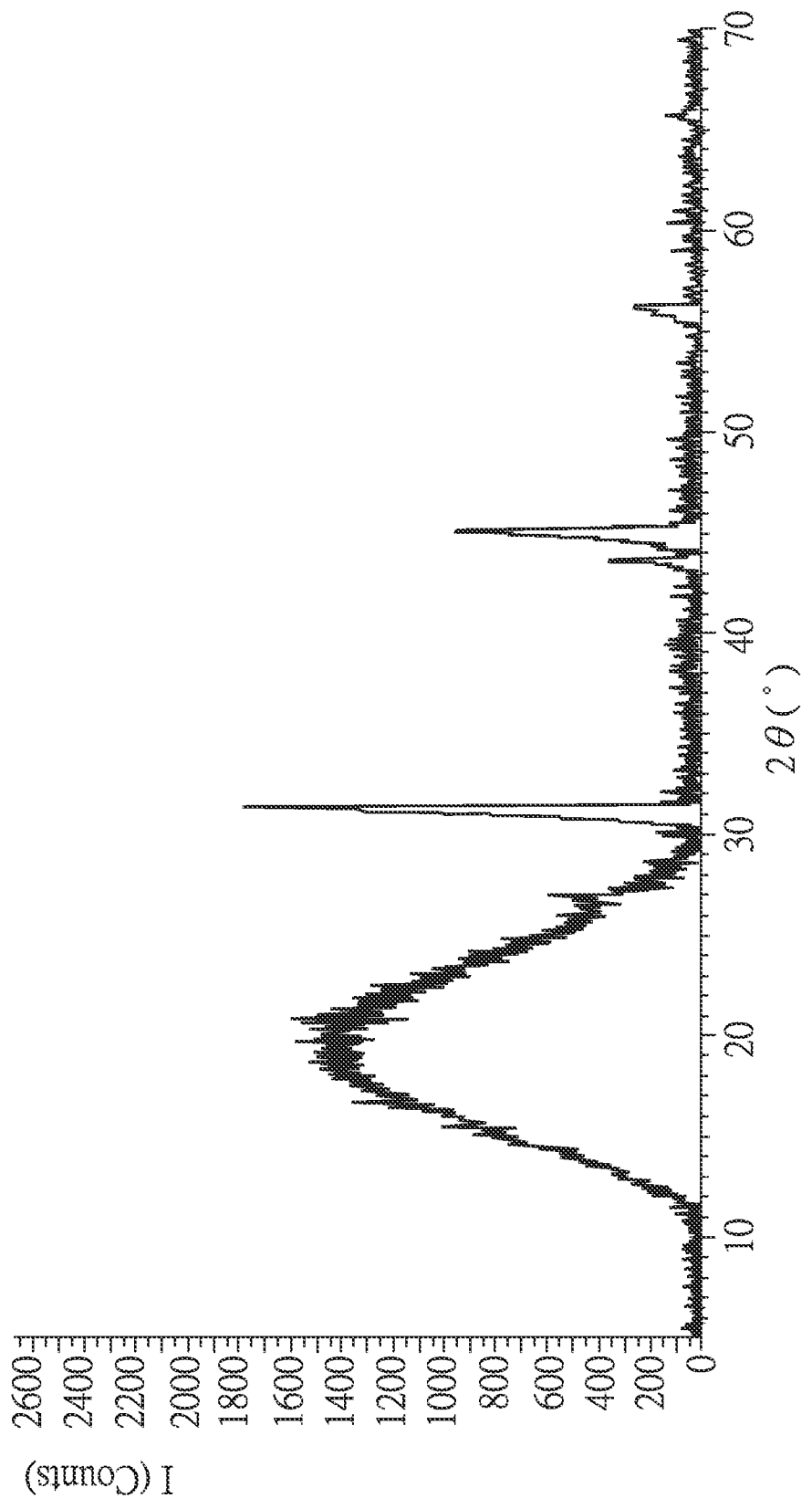
FIG. 8 shows an XRD pattern of a potassium salt of a compound of formula (2) according to Example 15 of the present disclosure.

The XRD pattern of the obtained potassium salt of the compound of Formula (2) is shown in FIG. 8. No significant peaks were found in the DSC curve. In addition, the TGA result indicates a weight loss of about 4% from ambient temperature to about 325° C.

Example 16—Preparation of Magnesium Salt of Compound of Formula (2)

The Sodium salt of the compound of Formula (2) prepared in Example 13 (5 g, 2 eq.) was dissolved in DI water (70 mL) at 15-25° C., and then magnesium sulfate (0.59 g, 1 eq.) was added. The mixture was stirred for 12 h. and then the solution was filtered and washed with DI water (50 mL). The cake was dried by vacuum at 40-45° C. to afford the magnesium salt. Yield: 3 g.

The XRD pattern and DSC curve of the magnesium salt of the compound of Formula (2) in the present example were obtained by the similar methods used in Example 2.

Figure 9:
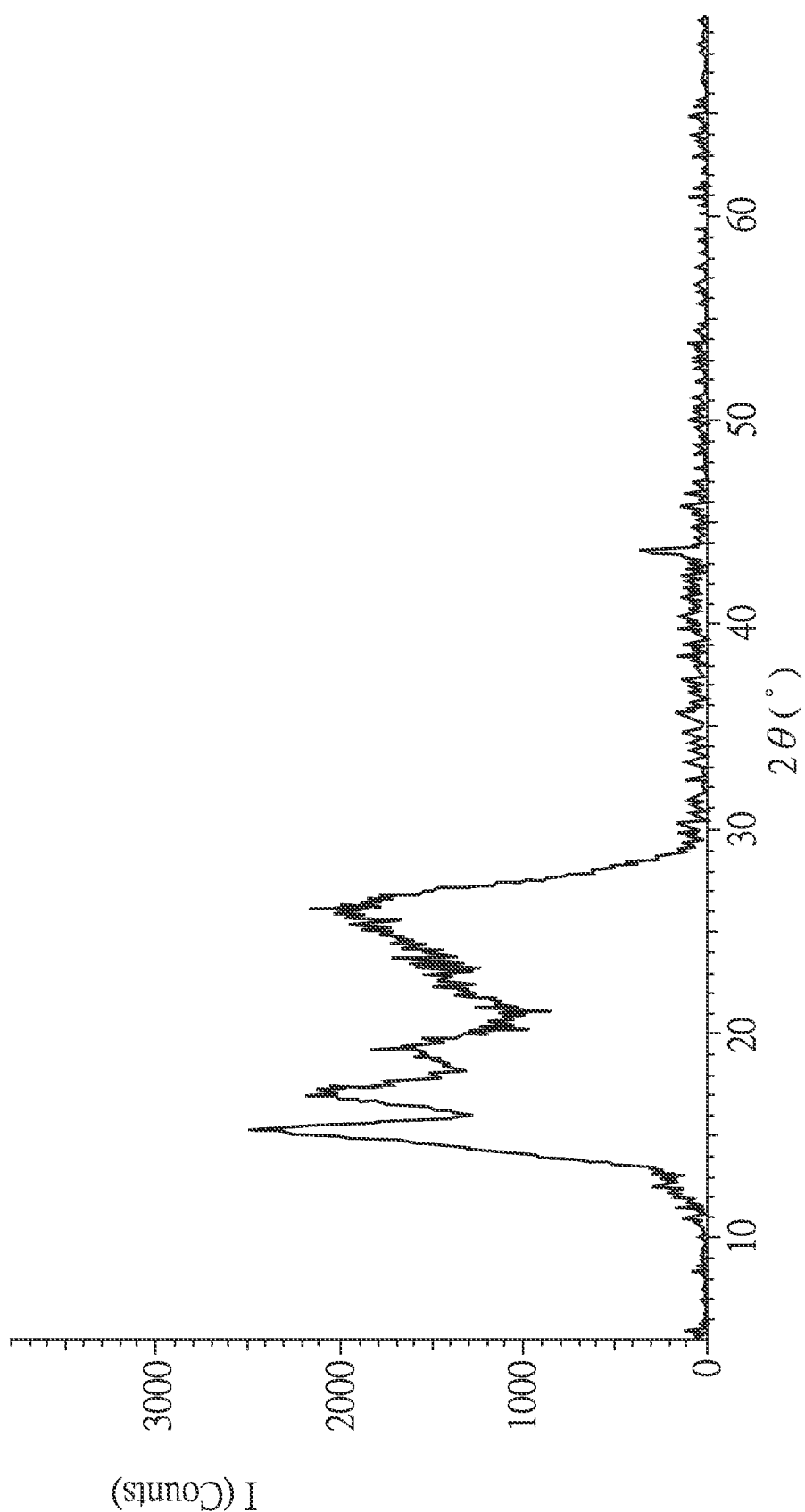
FIG. 9 shows an XRD pattern of a magnesium salt of a compound of formula (2) according to Example 16 of the present disclosure.

The XRD pattern of the obtained magnesium salt of the compound of Formula (2) is shown in FIG. 9. No significant peaks were found in the DSC curve. In addition, the TGA result indicates a weight loss of about 4% from ambient temperature to about 335° C.

Example 17—Preparation of Calcium Salt of Compound of Formula (2)

The Sodium salt of the compound of Formula (2) prepared in Example 13 (5.2 g, 2 eq.) was dissolved in DI water (70 mL) at 15-25° C. and then calcium chloride (0.57 g, 1 eq.) was added. The mixture was stirred for 12 h, and then the solution was filtered and washed with DI water (50 mL). The cake was dried by vacuum at 40-45° C. to afford the calcium salt. Yield: 2.5 g.

The XRD pattern and DSC curve of the calcium salt of the compound of Formula (2) in the present example were obtained by the similar methods used in Example 2.

Figure 10:
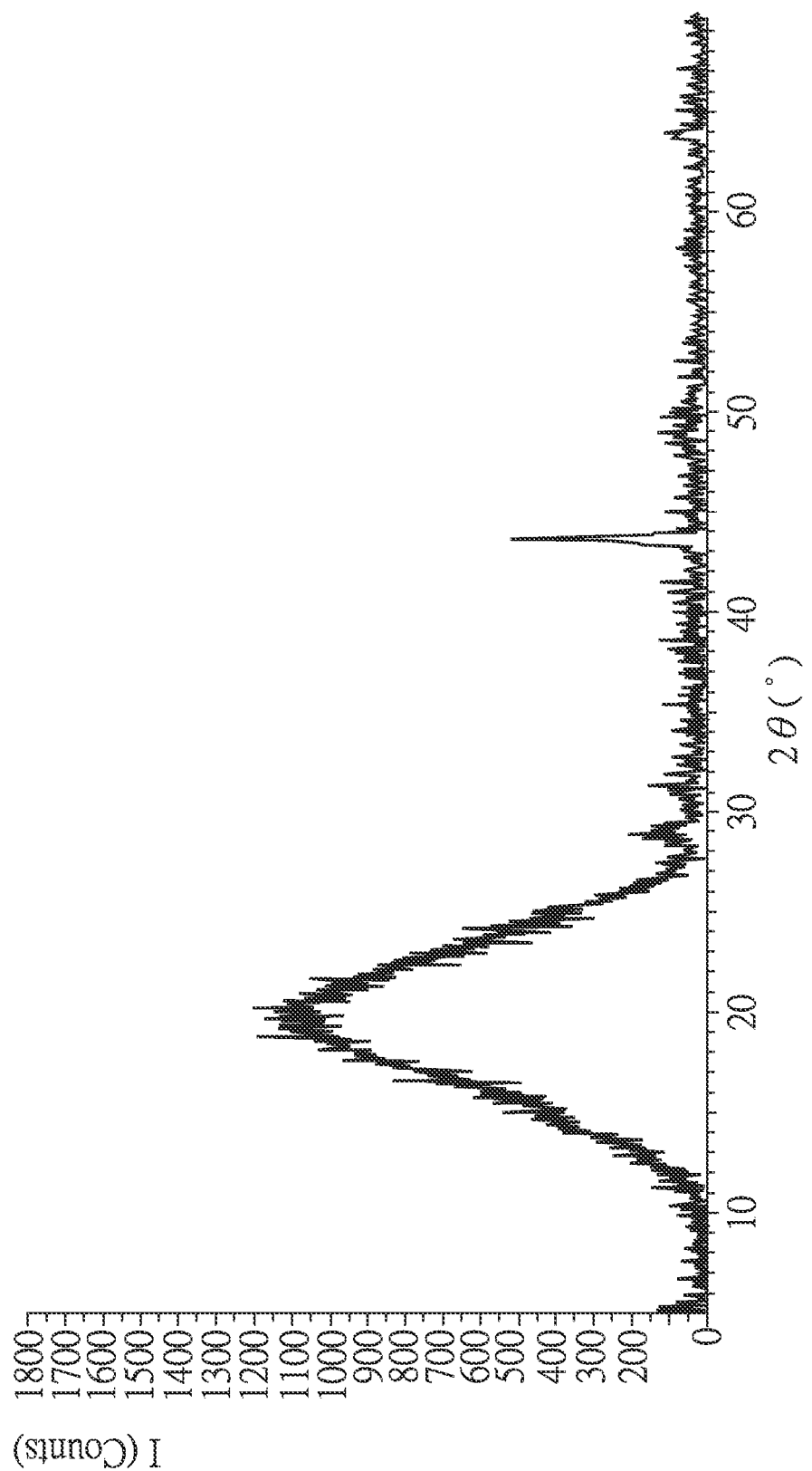
FIG. 10 shows an XRD pattern of a calcium salt of a compound of formula (2) according to Example 17 of the present disclosure.

The XRD pattern of the obtained calcium salt of the compound of Formula (2) is shown in FIG. 10. No significant peaks were found in the DSC curve. In addition, the TGA result indicates a weight loss of about 4% from ambient temperature to about 210° C.

Example 18—Preparation of Amorphous form of Compound of Formula (1)

Ethyl (S)-3-(4-((2-methyl-1-(4-(5-phenyl-1,3,4-oxadiazol-2-yl)phenyl)propyl)amino) benzamido)propanoate (10 g) was dissolved in Acetone (30 mL) and then dried by rotavaporary at 30° C. to afford the amorphous form. Yield: 9.5 g.

The XRD pattern and DSC curve of the amorphous form of the compound of Formula (1) in the present example were obtained by the similar methods used in Example 2.

The XRD pattern of the obtained amorphous form of the compound of Formula (1) is shown in FIG. 11. In addition, no significant peaks were found in the DSC curve.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:
1. A crystalline form of a compound of formula (1),

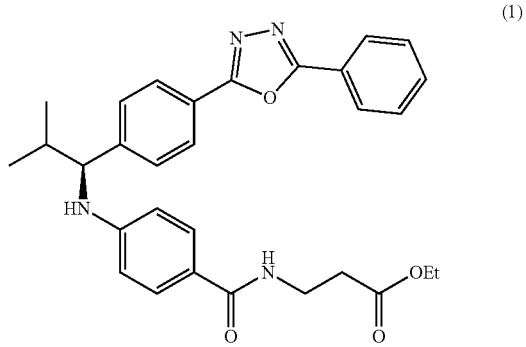 [SMILES: CCOC(=O)CCNC(=O)c1ccc(N[C@H](c2ccc(-c3nnc(-c4ccccc4)o3)cc2)C(C)C)cc1]

characterized by an X-ray diffraction (XRD) pattern having peaks at about 14.2, 15.6, 16.4, 20.1, 20.5 and 21.2°±0.2° 2θ.

2. The crystalline form of claim 1, wherein the XRD pattern further has peaks at about 17.4, 21.7 or 23.7°±0.2° 2θ.

3. The crystalline form of claim 1, wherein the XRD pattern is substantially as depicted in any of FIG. 1 to FIG. 4.

4. A crystalline form of a compound of formula (2),

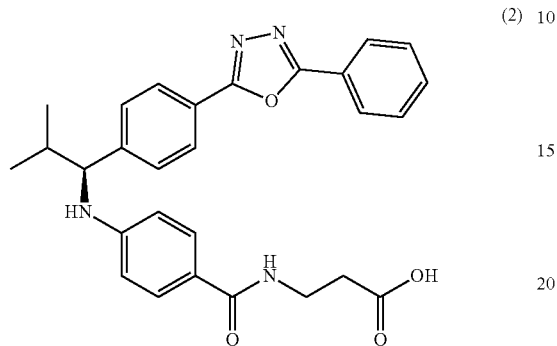

characterized by an XRD pattern having peaks at about 14.5, 18.6, 20.1, 21.8, 23.8, 25.0°±0.2° 2θ.

5. The crystalline form of claim 4, wherein the XRD pattern further has peaks at about 19.9, 22.0, 28.5 or 31.0°±0.2° 2θ.

6. The crystalline form of claim 4, wherein the XRD pattern is substantially as depicted in FIG. 5 or FIG. 6.

* * * * *